(12) United States Patent
Bjergarde et al.

(10) Patent No.: US 8,058,290 B2
(45) Date of Patent: Nov. 15, 2011

(54) 7-SUBSTITUTED AZA-INDAZOLES, COMPOSITIONS CONTAINING SAME, PRODUCTION METHOD AND USE THEREOF

(75) Inventors: Kirsten Bjergarde, Tucson, AZ (US); Anil Nair, Tucson, AZ (US); Marcel Patek, Tucson, AZ (US); Martha Ackerman-Berrier, Tucson, AZ (US); Martin Smrcina, Tucson, AZ (US); Eric Bacque, Gif sur Yvette (FR); Michel Tabart, La Norville (FR); Baptiste Ronan, Clamart (FR); Vincent Leroy, Nogent sur Marne (FR); Fabrice Viviani, Avenheim (FR); Mark Dodson, Oro Valley, AZ (US); Catherine Souaille, Choisy le Roi (FR)

(73) Assignee: Aventis Pharma S.A., Antony (FR)

( * ) Notice: Subject to any disclaimer, the term of this patent is extended or adjusted under 35 U.S.C. 154(b) by 300 days.

(21) Appl. No.: 12/021,638

(22) Filed: Jan. 29, 2008

(65) Prior Publication Data

US 2008/0182844 A1 Jul. 31, 2008

Related U.S. Application Data

(63) Continuation of application No. PCT/FR2005/001861, filed on Aug. 1, 2006.

(30) Foreign Application Priority Data

Aug. 4, 2005 (FR) ...................................... 05 08316

(51) Int. Cl.
*A61K 31/44* (2006.01)
*C07D 491/02* (2006.01)

(52) U.S. Cl. .......................... 514/303; 514/253; 546/119

(58) Field of Classification Search .................. 514/303, 514/253; 546/119
See application file for complete search history.

(56) References Cited

U.S. PATENT DOCUMENTS

| 6,562,811 | B1 | 5/2003 | Murata et al. | |
|---|---|---|---|---|
| 2004/0052822 | A1* | 3/2004 | Kohara et al. | 424/280.1 |
| 2004/0092546 | A1 | 5/2004 | Wei et al. | |
| 2004/0255397 | A1 | 12/2004 | Fessmann et al. | |
| 2007/0161626 | A1 | 7/2007 | Halley | |

FOREIGN PATENT DOCUMENTS

| DE | 25 38 950 | | 3/1977 |
|---|---|---|---|
| DE | 27 01 610 | | 7/1978 |
| DE | 0154 538 | | 3/1982 |
| EP | 1 876 178 | A1 | 1/2008 |
| GB | 1 302 287 | | 1/1973 |
| GB | 1 594 384 | | 7/1981 |
| JP | 4-117362 | | 4/1992 |
| WO | WO 01/19828 | A2 | 3/2001 |
| WO | WO 02/12242 | A2 | 2/2002 |
| WO | WO 03/008405 | A1 | 1/2003 |
| WO | WO 03/027095 | A1 | 4/2003 |
| WO | WO 03/045949 | A1 | 6/2003 |
| WO | WO 2004/009596 | A2 | 1/2004 |
| WO | WO 2004/076450 | A1 | 9/2004 |
| WO | WO 2004/096130 | A2 | 11/2004 |
| WO | WO 2005/009389 | A2 | 2/2005 |
| WO | WO 2005/063768 | A1 | 7/2005 |
| WO | WO 2005/073232 | A1 | 8/2005 |
| WO | WO 2005/110410 | A2 | 11/2005 |
| WO | WO 2006/003276 | | 1/2006 |
| WO | WO 2006/076442 | A2 | 7/2006 |
| WO | WO 2006/077319 | A1 | 7/2006 |
| WO | WO 2006/099075 | A2 | 9/2006 |
| WO | WO 2006/118231 | A1 | 11/2006 |
| WO | WO 2007/056582 | A1 | 5/2007 |

OTHER PUBLICATIONS

Nagar et al., 2003, CAS: 139:6801.*
Zeiner et al., 1986, CAS: 104:69338.*
Sennitskaya et al., 1977, CAS: 87:83993.*
U.S. Appl. No. 11/778,870, filed Jul. 17, 2007, Ronan.
Holland et al, Heterocyclic Tetrazoles, a New Class of Lipolysis Inhibitors, J. Med. Chem., 1967, 10(2), pp. 149-154.
Nagar et al, Facile Generation of Pyridopyrazoles: Synthesis of 3-amino-4-aryl-6-(p-benzoylaminophenyl)-pyrido-[2,3-d]-1-H-pyrazoles, J. Inst. Chemists (India), 2002, 74(4), pp. 129-131.
Reimann et al, Conformationally Restricted Pethidine Analogs, Part 6: Synthesis and Pharmacological Testing of Trans-octahydrobenzo[g]isoquinoline, Sci. Pharm., 1996, 64, pp. 637-646.
Reimann et al, English Translation of: Conformationally Restricted Pethidine Analogues, Part 6: Synthesis and Pharmacological Testing of Trans-octahydrobenzo[g]isoquinoline, Sci. Pharm., 1996, 64, pp. 637-646.
Sarkar et al, A Pummerer-based Generation and Trapping of furo[3,4-c]pyridines: an Approach to Nitrogen Containing Heterocyclic Analogues of 1-arylnaphthalene Lignans, Tetrahedron Letters, 2002, 43, pp. 1341-1344.
Sennitskaya et al, English Translation of: Structural Study of Indazoles, Pyrazolo[3,4-b]pyridines and Pyrazolo[3,4-b]pyrazine Using IR Spectroscopy, Chemistry of Heterocyclic Compounds, 1977, (5), pp. 662-667.

(Continued)

*Primary Examiner* — Rei-tsang Shiao
(74) *Attorney, Agent, or Firm* — Scully, Scott, Murphy & Presser, P.C.

(57) ABSTRACT

The disclosure relates to compounds of formula (I):

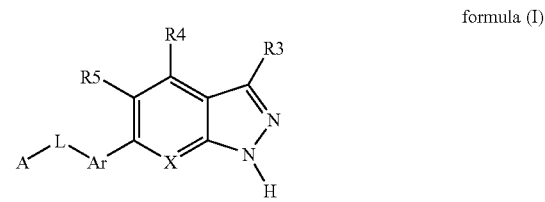

formula (I)

which modulate the activity of proteins, particularly kinases, and to compositions containing the same, and to the use thereof as medicaments, in particular as anticancer agents.

32 Claims, No Drawings

OTHER PUBLICATIONS

Sennitskaya et al, Structural Study of Indazoles, Pyrazolo[3,4-b]pyridines and Pyrazolo[3,4-b]pyrazine Using IR Spectroscopy, Chemistry of Heterocyclic Compounds, 1977, (5), pp. 662-667.

Szczepankiewicz et al, Aminopyridine-Based c-Jun N-Terminal Kinase Inhibitors with Cellular Activity and Minimal Cross-Kinase Activity, J. Med. Chem. 2006, 49, pp. 3563-3580.

Toshiharu et al, Pyridine Derivative, Salt Thereof and Insecticide and Acaricide Containing the Same Substance as Active Ingredient, Patent Abstracts of Japan, Publication No. 04117362, Publication Date: Apr. 17, 1992.

U.S. Appl. No. 13/084,077, filed Apr. 11, 2011.

* cited by examiner

7-SUBSTITUTED AZA-INDAZOLES, COMPOSITIONS CONTAINING SAME, PRODUCTION METHOD AND USE THEREOF

The present invention relates especially to novel chemical compounds, in particular novel substituted 7-azaindazoles, to compositions containing them, and to their use as medicaments.

More particularly, the invention relates to novel specific 7-azaindazoles which exhibit an anticancer activity, via the modulation of the activity of proteins, in particular of kinases.

To date, most of the commercial compounds used in chemotherapy pose considerable problems of side effects and of tolerance by the patients. These effects could be limited in so far as the medicaments used act selectively on cancer cells, and not on normal cells. One of the solutions for limiting the adverse effects of chemotherapy can therefore consist of the use of medicaments which act on metabolic pathways or elements which constitute these pathways, expressed predominantly in cancer cells, and which will be expressed little or not at all in normal cells.

Protein kinases are a family of enzymes which catalyse the phosphorylation of hydroxyl groups of specific residues of proteins, such as tyrosine, serine or threonine residues. Such phosphorylations can greatly modify the function of proteins; thus, protein kinases play an important role in the regulation of a large variety of cell processes, including in particular metabolism, cell proliferation, cell differentiation, cell migration or cell survival. Among the various cellular functions in which the activity of a protein kinase is involved, certain processes represent attractive targets for treating cancerous diseases and other diseases.

Thus, one of the objects of the invention is to provide compositions which have an anticancer activity, by acting in particular with respect to kinases. Among the kinases for which a modulation of activity is desired, FAK, KDR and Tie2 are preferred.

These products correspond to formula (I) below:

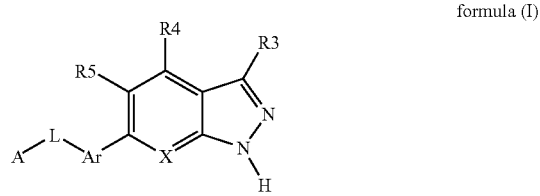

formula (I)

in which:
1) A and Ar are independently selected from the group consisting of: aryl, heteroaryl, heterocyclyl, substituted aryl, substituted heteroaryl, substituted heterocyclyl, cycloalkyl and substituted cycloalkyl;
2) L is selected from the group consisting of: NH, NH—SO$_2$, SO$_2$NH, NH—CH$_2$, CH$_2$—NH, NH—CO, CO—NH, CH$_2$—CO—NH, NH—CO—CH$_2$, NH—CH$_2$—CO, CO—CH$_2$—NH, NH—CO—NH, NH—CS—NH, NH—CO—O, O—CO—NH, CH$_2$—NH—CO—NH, NH—CO—NH—CH$_2$ and NH—CO—CH$_2$—CO—NH;
3) X is N or NO;
4) R3 is selected from the group consisting of H and NHMR"3, in which M is selected from the group consisting of: a bond, CO, CO—NH, CS, CS—NH and SO$_2$; and in which R"3 is selected from the group consisting of: H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl;
5) R4 is selected from the group consisting of: H, halogen, alkyl, substituted alkyl, OR"4, N(R"5)(R"6) CON(R"5)(R"6), in which R"4 is chosen from H, phenyl, substituted phenyl, alkyl, substituted alkyl, and in which R"5 and R"6 are independently selected from the group consisting of H, (C$_1$-C$_6$)alkyl, substituted (C$_1$-C$_6$)alkyl, —(C$_1$-C$_6$)alkylheterocyclyl, substituted —(C$_1$-C$_6$)alkylheterocyclyl, —(C$_1$-C$_6$)alkylheteroaryl, substituted —(C$_1$-C$_6$)alkylheteroaryl, cycloalkyl, substituted cycloalkyl, heterocyclyl, substituted heterocyclyl, aryl, substituted aryl, heteroaryl, substituted heteroaryl, or else R"5 and R"6 are linked to one another so as to form a saturated ring having from 4 to 8 ring members containing from 1 to 3 hetero atoms chosen from O, S and N, optionally substituted;
6) R5 is selected from the group consisting of: H, halogen, R'2, CN, O(R'2), OC(O)(R'2), OC(O)N(R'2)(R'3), OS(O$_2$)(R'2), N(R'2)(R'3), N=C(R'2)(R'3), N(R'2)C(O)(R'3), N(R'2)C(O)O(R'3), N(R'4)C(O)N(R'2)(R'3), N(R'4)C(S)N(R'2)(R'3), N(R'2)S(O$_2$)(R'3), C(O)(R'2), C(O)O(R'2), C(O)N(R'2)(R'3), C(=N(R'3))(R'2), C(=N(OR'3))(R'2), S(R'2), S(O)(R'2), S(O$_2$)(R'2), S(O$_2$)O(R'2), S(O$_2$)N(R'2)(R'3); in which each R'2, R'3, R'4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, substituted heterocyclyl; and R'2 and R'3 can be linked to one another so as to form a ring containing from 1 to 3 hetero atoms chosen from O, S and N;

provided that, when X is N, R3 is NH$_2$, Ar and A are unsubstituted phenyl, L is NHCO linked in the para-position with respect to Ar, and R5 is H, then R4 is not chosen from: phenyl, o-chlorophenyl, cinnamyl, α-furfuryl, o-hydroxyphenyl, p-hydroxy-m-methoxyphenyl, p-methylthiophenyl, p-methoxyphenyl, o-nitrophenyl, m-phenoxyphenyl, and provided that, when X is N, R5 is H, R4 is H, and Ar-L-A is a group

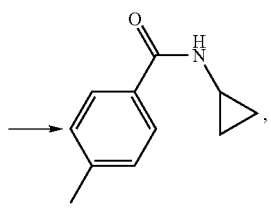

then R3 is not chosen from: amino, acetylamino, [(4-fluorophenyl)carbonyl]amino, (2-methylpropanoyl)amino, -(cyclopentylcarbonyl)amino, propanoylamino, [(4-methylphenyl)carbonyl]amino, {[4-(methyloxy)phenyl]carbonyl}amino, (2-thienylcarbonyl)amino, (methylsulphonyl)amino, -[(4-fluorophenyl)sulphonyl]amino, (ethylsulphonyl)amino, (propylsulphonyl)amino, (3-thienylsulphonyl)amino, [(3,5-dimethyl-4-isoxazolyl)sulphonyl]amino, (2-thienylsulphonyl)amino and (1-methylethyl)amino.

Products of formula (I) that are preferred correspond to the following definition:

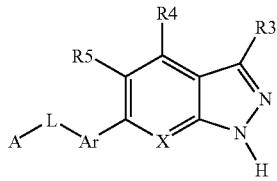

formula (I)

in which:
1) A and Ar are independently selected from the group consisting of: aryl, heteroaryl, heterocyclyl, cycloalkyl, substituted aryl, substituted heteroaryl, substituted heterocyclyl and substituted cycloalkyl;
2) L is selected from the group consisting of: NH, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH, CH$_2$—NH—CO—NH, NH—CO—NH—CH$_2$ and NH—CO—CH$_2$—CO—NH;
3) X is N;
4) R3 is selected from H, NH2 and NHCOR"3 and R"3 is selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl;
5) R4 is selected from the group consisting of: H, halogen, alkyl, substituted alkyl, CON(R"5)(R"6) in which R"5 and R"6 are independently selected from the group consisting of H, (C$_1$-C$_6$)alkyl, substituted (C$_1$-C$_6$)alkyl, —(C$_1$-C$_6$)alkylheterocyclyl, substituted —(C$_1$-C$_6$)alkylheterocyclyl, —(C$_1$-C$_6$)alkyheteroaryl, substituted —(C$_1$-C$_6$)alkylheteroaryl, cycloalkyl, substituted cycloalkyl, heterocyclyl, substituted heterocyclyl, aryl, substituted aryl, heteroaryl, substituted heteroaryl or else R"5 and R"6 are linked to one another so as to form a saturated ring having from 4 to 8 ring members containing from 1 to 3 hetero atoms chosen from O, S and N, optionally substituted;
6) R5 is H.

In the products of formula (I), Ar is chosen from a thiazolyl, thienyl, furyl, pyrrolyl, oxazolyl, isoxazolyl, isothiazolyl, thiadiazolyl, pyrazolyl, imidazolyl, indolyl, indazolyl, benzimidazolyl, benzoxazolyl and benzothiazolyl; optionally substituted, or else Ar is a thiazolyl, or else Ar-L-A is:

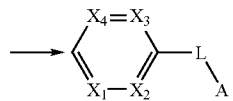

in which X1, X2, X3 and X4 is independently chosen from N and C—R'5, in which R'5 has the same definition as R5.

L-A substituents which are preferred are advantageously chosen from NH—CO—NH-A and NH—SO$_2$-A. A particularly effective L-A combination is obtained when L-A is NHCONH-A.

Products in accordance with the invention preferably have an A substituent which is selected from the group consisting of phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl; optionally substituted.

More preferably, A is chosen from phenyl, pyrazolyl and isoxazolyl; optionally substituted.

The A substituent is very advantageously substituted with a first substituent selected from the group consisting of halogen, alkyl, alkylene, alkynyl, aryl, heteroaryl, O-alkyl, O-aryl, O-heteroaryl, S-alkyl, S-aryl, S-heteroaryl, each being optionally substituted with one or more substituents chosen from (C$_1$-C$_3$)alkyl, halogen and O—(C$_1$-C$_3$)alkyl.

The A substituent is preferably substituted with a second substituent chosen from the group consisting of F, Cl, Br, I, OH, SH, SO$_3$M, COOM, CN, NO$_2$, CON(R8)(R9), N(R8)CO(R9), (C$_1$-C$_3$)alkyl-OH, (C$_1$-C$_3$)alkyl-N(R8)(R9), (C$_1$-C$_3$)alkyl-(R10), (C$_1$-C$_3$)alkyl-COOH, N(R8)(R9); in which R8 and R9 are independently chosen from H, (C$_1$-C$_3$)alkyl, halogenated (C$_1$-C$_3$)alkyl, (C$_1$-C$_3$)alkylOH, (C$_1$-C$_3$)alkyl-O(C$_1$-C$_3$)alkyl, (C$_1$-C$_3$)alkylNH$_2$, (C$_1$-C$_3$)alkylN(R8)(R9), (C$_1$-C$_3$)alkylCOOM, (C$_1$-C$_3$)alkylSO$_3$M; in which, when R8 and R9 are simultaneously different from H, they can be linked so as to form a ring having from 5 to 7 ring members containing from 1 to 3 hetero atoms; in which M is H or a cation of an alkali metal chosen from Li, Na and K; and in which R10 is H or an optionally substituted, non-aromatic heterocycle containing 2 to 7 carbon atoms and 1 to 3 hetero atoms chosen from N, O and S.

A substituents which are particularly preferred are chosen from phenyl, pyrazolyl and isoxazolyl; it being possible for said A substituents to be substituted with halogen, (C$_1$-C$_4$) alkyl, halogenated (C$_1$-C$_3$)alkyl, O—(C$_1$-C$_4$)alkyl, S—(C$_1$-C$_4$)alkyl, halogenated O—(C$_1$-C$_4$)alkyl, and halogenated S—(C$_1$-C$_4$)alkyl. When A is disubstituted, the two substituents of A can form a ring having from 5 to 7 ring members containing from 0 to 3 hetero atoms chosen from O, N and S.

An R4 substituent is advantageously selected from the group consisting of H and CON(R"5)(R"6), with R"5 and R"6 as defined above.

A product in accordance with the invention may be in:
a) non-chiral form, or
b) racemic form, or
c) a form enriched in a stereoisomer, or
d) a form enriched in an enantiomer;
and may be optionally salified.

A product in accordance with the invention may be used for the manufacture of a medicament for use in the treatment of a pathological condition, in particular a cancer. A subject of the present invention is a medicament, characterized in that it comprises a product of formula (I) or an addition salt of this compound with a pharmaceutically acceptable acid, or else a hydrate or a solvate of the product of formula (I).

The present invention also relates to the therapeutic compositions comprising a product according to the invention, in combination with a pharmaceutically acceptable excipient according to the method of administration selected. The pharmaceutical composition can be in solid or liquid form or in the form of liposomes.

Among the solid compositions, mention may be made of powders, gelatin capsules and tablets. Among the oral forms, solid forms protected against the acidic medium of the stomach can also be included. The carriers used for the solid forms consist in particular of mineral carriers such as phosphates or carbonates, or of organic carriers such as lactose, celluloses, starch or polymers. The liquid forms consist of solutions, of suspensions or of dispersions. As dispersive carrier they contain either water or an organic solvent (ethanol, NMP, or the like), or mixtures of surfactants and solvents or of complexing agents and solvents.

The liquid forms will preferably be injectable and, as a result, will have a formulation that is acceptable for such a use.

Acceptable routes of administration by injection include intravenous, intraperitoneal, intramuscular and subcutaneous routes, the intravenous route usually being preferred.

The administered dose of the compounds of the invention will be adjusted by the practitioner according to the route of administration for the patient and the condition of the latter.

By virtue of their low toxicity and their pharmacological and biological properties, the compounds of the present invention find their application in the treatment of any carcinoma having a considerable degree of vascularization or inducing metastases, or, finally, in pathologies of lymphoma and leukaemia type.

These compounds represent a therapy of choice, either alone or in combination with suitable chemotherapy or radiotherapy, and/or in combination with other compounds having anti-angiogenic activities, such as VEGF inhibitors or FGF inhibitors. Thus, the products of general formula (I) are in particular of use for the treatment or prevention of a pathological condition characterized in that the product is administered alone or in combination with other active ingredients, in particular anticancer agents such as cytotoxic, cytostatic, anti-angiogenic or anti-metastatic products.

The compounds of the present invention can therefore be administered alone or as a mixture with other anticancer agents. Among the possible combinations, mention may be made of:

- alkylating agents, and in particular cyclophosphamide, melphalan, ifosfamide, chlorambucil, busulphan, thiotepa, prednimustine, carmustine, lomustine, semustine, steptozotocin, decarbazine, temozolomide, procarbazine and hexamethylmelamine;
- platinum derivatives, such as in particular cisplatin, carboplatin or oxaliplatin;
- antibiotics, such as in particular bleomycin, mitomycin or dactinomycin;
- antimicrotubule agents, such as in particular vinblastine, vincristine, vindesine, vinorelbine, taxoides (paclitaxel and docetaxel);
- anthracyclines, such as in particular doxorubicin, daunorubicin, idarubicin, epirubicin, mitoxantrone or losoxantrone;
- group I and II topoisomerase inhibitors, such as etoposide, teniposide, amsacrine, irinotecan, topotecan and tomudex;
- fluoropyrimidines such as 5-fluorouracil, UFT orfloxuridine;
- cytidine analogues such as 5-azacytidine, cytarabine, gemcitabine, 6-mercaptomurine or 6-thioguanine;
- adenosine analogues such as pentostatin, cytarabine or fludarabine phosphate;
- methotrexate and folinic acid;
- various enzymes and compounds, such as L-asparaginase, hydroxyurea, trans-retinoic acid, suramin, dexrazoxane, amifostine, herceptin, and also oestrogenic and androgenic hormones;
- antivascular agents, such as combretastatin derivatives, for example CA4P, chalcones or colchicine, for example ZD6126, and their prodrugs;
- anti-angiogenic agents, such as bevacizumab, sorafenib or sunitinib malate;
- therapeutic agents which inhibit other tyrosine kinases, such as imatinib, gefitinib and erlotinib.

When the compounds of the present invention are combined with another treatment or with a radiation treatment, these treatments can then be administered simultaneously, separately or sequentially. The treatment will be adjusted by the practitioner according to the disease to be treated.

The products of the invention are of use as agents for inhibiting a reaction catalysed by one or more kinases. FAK, KDR and Tie2 are kinases for which the products of the invention will be particularly useful as inhibitors.

The reasons for which these kinases are chosen are given hereinafter:

FAK

FAK is a cytoplasmic tyrosine kinase which plays an important role in transduction of the signal transmitted by integrins, a family of heterodimeric cell adhesion receptors. FAK and the integrins are located in perimembrane structures called adhesion plaques. It has been shown, in many cell types, that the activation of FAK and also the phosphorylation thereof on tyrosine residues, and in particular the autophosphorylation thereof on tyrosine 397, depend on binding of the integrins to their extracellular ligands, and are therefore induced during cell adhesion [Kornberg L, et al. J. Biol. Chem. 267(33): 23439-442. (1992)]. The autophosphorylation of FAK on tyrosine 397 represents a binding site for another tyrosine kinase, Src, via its SH2 domain [Schaller et al. Mol. Cell. Biol. 14:1680-1688. 1994; Xing et al. Mol. Cell. Biol. 5:413-421. 1994]. Src can then phosphorylate FAK on tyrosine 925, thus recruiting the Grb2 adaptor protein and inducing, in certain cells, activation of the ras and MAP kinase pathway involved in the control of cell proliferation [Schlaepfer et al. Nature; 372:786-791. 1994; Schlaepfer et al. Prog. Biophy. Mol. Biol. 71:435-478. 1999; Schlaepfer and Hunter, J. Biol. Chem. 272:13189-13195. 1997]. The activation of FAK can also induce the jun $NH_2$-terminal kinase (JNK) signalling pathway and result in the progression of cells to the G1 phase of the cell cycle [Oktay et al., J. Cell. Biol. 145:1461-1469. 1999]. Phosphatidylinositol-3-OH kinase (PI3-kinase) also binds to FAK on tyrosine 397 and this interaction could be necessary for the activation of PI3-kinase [Chen and Guan, Proc. Nat. Acad. Sci. USA. 91:10148-10152. 1994; Ling et al. J. Cell. Biochem. 73:533-544. 1999]. The FAK/Src complex phosphorylates various substrates such as paxillin and p130CAS in fibroblasts [Vuori et al. Mol. Cell. Biol. 16: 2606-2613. 1996].

The results of many studies support the hypothesis that FAK inhibitors could be useful in the treatment of cancer. Studies have suggested that FAK could play an important role in cell proliferation and/or survival in vitro. For example, in CHO cells, certain authors have demonstrated that the overexpression of p125FAK results in an acceleration of G1 to S transition, suggesting that p125FAK promotes cell proliferation [Zhao J.-H et al. J. Cell Biol. 143:1997-2008. 1998]. Other authors have shown that tumour cells treated with FAK antisense oligonucleotides lose their adhesion and enter into apoptosis (Xu et al, Cell Growth Differ. 4:413-418. 1996). It has also been demonstrated that FAK promotes cell migration in vitro. Thus, fibroblasts deficient for FAK expression (FAK « knockout »mice) exhibit a rounded morphology and deficiencies in cell migration in response to chemotactic signals, and these deficiencies are eliminated by re-expression of FAK [D J. Sieg et al., J. Cell Science. 112:2677-91. 1999]. Overexpression of the C-terminal domain of FAK (FRNK) blocks elongation of adherent cells and reduces cell migration in vitro [Richardson A. and Parsons J. T. Nature. 380:538-540. 1996]. Overexpression of FAK in CHO or COS cells or in human astrocytoma cells promotes cell migration. The involvement of FAK in promoting proliferation and migration of cells in many cell types in vitro suggests a potential role for FAK in neoplastic processes. A recent study has effectively demonstrated an increase in tumour cell proliferation in vivo after induction of FAK expression in human astrocytoma cells [Cary L. A. et al. J. Cell Sci. 109:1787-94. 1996; Wang D et al. J. Cell Sci. 113:4221-4230. 2000]. In addition, immunohistochemical studies of human biopsies have demonstrated that FAK is overexpressed in prostate cancers, breast cancers, thyroid cancers, colon cancers, melanomas, brain cancers and lung cancers, the level of expression of FAK being directly correlated with the tumours exhibiting the most aggressive phenotype [Weiner T M, et al. Lancet. 342(8878):1024-1025. 1993; Owens et al. Cancer Research. 55:2752-2755. 1995; Maung K. et al. Oncogene. 18:6824-6828. 1999; Wang D et al. J. Cell Sci. 113:4221-4230. 2000].

KDR

KDR (Kinase insert Domain Receptor), also called VEGF-R2 (Vascular Endothelial Growth Factor Receptor 2), is expressed only in endothelial cells. This receptor binds to the angiogenic growth factor VEGF, and thus serves as a mediator for a transduction signal via activation of its intracellular kinase domain. Direct inhibition of the kinase activity of VEGF-R2 makes it possible to reduce the phenomenon of angiogenesis in the presence of exogenous VEGF (Vascular Endothelial Growth Factor) (Strawn et al., *Cancer Research*, 1996, vol. 56, p. 3540-3545). This process has been demonstrated in particular by means of VEGF-R2 mutants (Millauer et al., *Cancer Research*, 1996, vol. 56, p. 1615-1620). The VEGF-R2 receptor seems to have no function in adults other than that related to the angiogenic activity of VEGF. Consequently, a selective inhibitor of the kinase activity of VEGF-R2 should show only slight toxicity.

In addition to this central role in the dynamic angiogenic process, recent results suggest that VEGF expression contributes to tumour cell survival after chemotherapy and radiotherapy, underlining the potential synergy of KDR inhibitors with other agents (Lee et al. *Cancer Research*, 2000, vol. 60, p. 5565-5570).

Tie2

Tie-2 (TEK) is a member of a family of tyrosine kinase receptors, specific for endothelial cells. Tie2 is the first receptor with tyrosine kinase activity for which both the agonist (angiopoietin 1 or Ang1), which stimulates autophosphorylation of the receptor and cell signalling [S. Davis et al. (1996) *Cell* 87, 1161-1169], and the antagonist (angiopoietin 2 or Ang2) [P. C. Maisonpierre et al. (1997) *Science* 277, 55-60] are known. Angiopoietin 1 can synergize with VEGF in the final stages of neoangiogenesis [*Asahara T. Circ. Res.* (1998) 233-240]. Knockout experiments and transgenic manipulations of Tie2 expression or of Ang1 expression result in animals which exhibit vascularization deficiencies [D. J. Dumont et al. (1994) *Genes Dev.* 8, 1897-1909 and C. Suri (1996) *Cell* 87, 1171-1180]. The binding of Ang1 to its receptor results in autophosphorylation of the kinase domain of Tie2, which is essential for neovascularization and for the recruitment and the interaction of the vessels with the pericytes and the smooth muscle cells; these phenomena contribute to the maturation and stability of the newly formed vessels [P. C. Maisonpierre et al. (1997) *Science* 277, 55-60]. Lin et al. (1997), *J. Clin. Invest.* 100, 8: 2072-2078 and Lin P. (1998), *PNAS* 95, 8829-8834, have shown an inhibition of tumour growth and vascularization, and also a decrease in lung metastases, during adenoviral infections or injections of the extracellular domain of Tie-2 (Tek) in melanoma and breast tumour xenograph models.

For the following reasons, Tie2 inhibitors can be used in situations where neovascularization or angiogenesis occurs inappropriately, i.e. in cancers in general, but also in specific cancers such as Kaposi's sarcoma or infantile haemangioma, rheumatoid arthritis, osteoarthritis and/or associated pain, inflammatory diseases of the intestine, such as ulcerative collitis or Crohn's disease, pathologies of the eye, such as age-related macular degeneration, diabetic retinopathies, chronic inflammation, or psoriasis.

Angiogenesis is a process for generating new blood vessels from pre-existing vessels. Tumour angiogenesis (formation of blood neovessels), which is essential for tumour growth, is also one of the essential factors of metastatic dissemination (Oncogene. 2003 May 19; 22(20):3172-9; Nat Med. 1995 January; 1(1):27-31.).

This neovascularization is due to the migration, then to the proliferation and differentiation, of the endothelial cells under the influence of angiogenic factors secreted by the cancer cells and the cells of the stroma (Recent Prog Horm Res. 2000; 55:15-35; 35-6).

The angiopoietin 1/Tie2 receptor system plays a predominant role in vessel maturation by allowing the recruitment of peri-endothelial cells so as to stabilize the vessel (Cell. 1996 Dec. 27; 87(7):1161-9, Recent Prog Horm Res. 2004; 59:51-71). It has thus been shown that administration of the soluble recombinant form of the extracellular domain of the Tie-2 receptor (exTek) inhibits tumour angiogenesis in murine tumour models and also metastatic development (Proc Natl Acad Sci USA. 1998 Jul. 21; 95(15):8829-34; Cancer immunol Immunother. 2004 July; 53(7):600-8). In endothelial cells in culture, stimulation of Tie-2 activates the PI3 kinase pathway and p42/p44 pathway, which pathways are involved in cell proliferation and migration; and the PAF synthesis pathway (Cell Signal. 2006 Apr. 14; ahead of print), which pathway is involved in pro-inflammatory activity. Tie2 stimulation stimulates the Akt pathway and inhibits apoptosis (Exp Cell Res. 2004 Aug. 1; 298(1):167-77), a transduction pathway known to be important in cell survival.

The addition of Extek (soluble receptor for Tie2) inhibits the formation of endothelial cell pseudotubules on Matrigel (Cancer immunol Immunother. 2004 July; 53(7): 600-8). These studies indicate that the Tie-2/angiopoietin system is necessary during the first stages of vascular bud formation in adult tissues and that one function of the Tie-2 receptor is to increase endothelial cell survival during blood vessel formation. In addition, angiopoietin-1 stimulates lymphatic endothelial cell proliferation and lymphangiogenesis (development of lymphatic neovessels), a preferred route of access for metastatic development (Blood. 2005 Jun. 15; 105(12): 4649-56).

The processes of angiogenesis thus play a predominant role in the progression of numerous solid tumours. In addition, it has been shown that the probability of appearance of metastases increases very greatly with an increase in vascularization of the primary tumour (Br J Cancer. 2002 May 20; 86(10): 1566-77).

The potential role of pro-angiogenic agents in leukaemias and lymphomas has also more recently been documented. In fact, in general, it has been reported that cell clones in these pathologies can be either naturally destroyed by the immune system or can switch into an angiogenic phenotype which promotes their survival and then their proliferation. This change in phenotype is induced by an overexpression of angiogenic factors, in particular by macrophages, and/or mobilization of these factors from the extracellular matrix (Thomas D A, Giles F J, Cortes J, Albitar M, Kantarjian H M., *Acta Haematol*, (2001), vol 207, pp 106-190).

A correlation exists between the process of angiogenesis in the bone marrow and "extramedullar disease" in CML (chronic myelomonocytic leukaemia). Various studies demonstrate that the inhibition of angiogenesis could represent a therapy of choice in this pathology (Leuk Res. 2006 January; 30(1): 54-9; Histol Histopathol. 2004 October; 19(4): 1245-60). In addition, it is strongly suggested that activation of the Tie2/angiopoietin system is involved in the development of angiogenesis in the bone marrow in patients suffering from multiple myeloma (Blood. 2003 Jul. 15; 102(2): 638-45).

Rheumatoid arthritis (RA) is a chronic disease with an unknown etiology. Although it affects many organs, the most severe form of RA is a progressive synovial inflammation of the joints resulting in destruction. Angiogenesis appears to considerably affect the progression of this pathology. Thus, it has been shown that Tie2 activation regulates angiogenesis in synovial tissues, promoting the development of rheumatoid arthritis (Arthritis Rheum. 2003 September; 48(9): 2461-71).

An overexpression of angiopoietin 1 and of Tie2 in the synovial tissues of patients suffering from osteoarthritis, correlated with an active neovascularization, has also been shown (Shahrara S et al. Arthritis Res. 2002; 4(3)). Thus, it has been shown that, by blocking Tie2 activation using an adenovirus producing exTEK (soluble Tie2 receptor), inhibition of angiogenesis and the development of arthrosis and protection against bone degradation are obtained in a mouse model in which arthrosis is induced with collagen (Arthritis Rheum. 2005 May; 52(5):1346-8).

IBD (inflammatory bowel disease) comprises two forms of chronic inflammatory diseases of the intestine: UC (ulcerative colitis) and Crohn's disease (CD). IBD is characterized by an immune dysfunction which results in an inappropriate production of inflammatory cytokines inducing the establishment of a local microvascular system. This angiogenesis of inflammatory origin results in intestinal ischaemia induced by vasoconstriction (Inflamm Bowel Dis. 2006 June; 12(6): 515-23).

Eye pathologies relating to neovascularization phenomena, such as age-related macular degeneration, are responsible for a large majority of cases of blindness in developed countries. The molecular signals which control neovascularization phenomena in the eye, such as VEGFs or angiopoietins, are targets of choice in these pathologies (Campochiaro P A. Expert Opin Biol Ther. 2004 September; 4(9)). It has thus been shown that blocking Tie2 activation using an adenovirus producing exTEK (soluble Tie2 receptor) inhibits the retinal and choroidal neovascularization which is the most common cause of loss of vision (Hum Gene Ther. 2001 Jul. 1; 12(10): 1311-21).

DEFINITIONS

The term « halogen » refers to an element chosen from F, Cl, Br, and I.

The term « alkyl » refers to a linear or branched, saturated hydrocarbon-based substituent having from 1 to 12 carbon atoms. Methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl substituents are examples of an alkyl substituent.

The term « alkylene » refers to a linear or branched hydrocarbon-based substituent having one or more unsaturations, and having from 2 to 12 carbon atoms. Ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methyldienylprop-2-enyl, Z-2-methylbut-1,3-dienyl, E-2-methylbut-1,3-dienyl, 2-methyl-1-methylidenylprop-2-enyl, undec-1-enyl and undec-10-enyl substituents are examples of an alkylene substituent.

The term « alkynyl » refers to a linear or branched hydrocarbon-based substituent having at least two unsaturations borne by a pair of vicinal carbon atoms, and having from 2 to 12 carbon atoms. Ethynyl, prop-1-ynyl, prop-2-ynyl and but-1-ynyl substituents are examples of an alkynyl substituent.

The term « aryl » refers to a mono- or polycyclic aromatic substituent having from 6 to 14 carbon atoms. Phenyl, naphth-1-yl, naphth-2-yl, anthracen-9-yl, 1,2,3,4-tetrahydronaphth-5-yl and 1,2,3,4-tetrahydronaphth-6-yl substituents are examples of an aryl substituent.

The term « heteroaryl » refers to a mono- or polycyclic heteroaromatic substituent having from 1 to 13 carbon atoms and from 1 to 4 hetero atoms. Pyrrol-1-yl, pyrrol-2-yl, pyrrol-3-yl, furyl, thienyl, imidazolyl, oxazolyl, thiazolyl, isoxazolyl, isothiazolyl, 1,2,4-triazolyl, oxadiazolyl, thiadiazolyl, tetrazolyl, pyridyl, pyrimidyl, pyrazinyl, 1,3,5-triazinyl, indolyl, benzo[b]furyl, benzo[b]thienyl, indazolyl, benzimidazolyl, azaindolyl, quinoleyl, isoquinoleyl, carbazolyl and acridyl substituents are examples of a heteroaryl substituent.

The term « hetero atom » refers here to an atom that is at least divalent, other than carbon. N, O, S and Se are examples of a hetero atom.

The term « cycloalkyl » refers to a saturated or partially unsaturated cyclic hydrocarbon-based substituent having from 3 to 12 carbon atoms. Cyclopropyl, cyclobutyl, cyclopentyl, cyclopentenyl, cyclopentadienyl, cyclohexyl, cyclohexenyl, cycloheptyl, bicyclo[2.2.1]heptyl; cyclooctyl, bicyclo[2.2.2]octyl; adamantyl and perhydronaphthyl substituents are examples of a cycloalkyl substituent.

The term « heterocyclyl » refers to a saturated or partially unsaturated cyclic hydrocarbon-based substituent having from 1 to 13 carbon atoms and from 1 to 4 hetero atoms. Preferably, the saturated or partially unsaturated cyclic hydrocarbon-based substituent will be monocyclic and will contain 4 or 5 carbon atoms and 1 to 3 hetero atoms.

The term « substituted » refers to one or more substituents other than H, for example halogen, alkyl, aryl, heteroaryl, cycloalkyl, heterocyclyl, alkylene, alkynyl, OH, O-alkyl, alkyl-OH, O-alkylene, O-aryl, O-heteroaryl, $NH_2$, NH-alkyl, NH-aryl, NH-heteroaryl, N-alkyl-alkyl', SH, S-alkyl, S-aryl, $S(O_2)H$, $S(O_2)$-alkyl, $S(O_2)$-aryl, $SO_3H$, $SO_3$-alkyl, $SO_3$-aryl, CHO, C(O)-alkyl, C(O)-aryl, C(O)OH, C(O)O-alkyl, C(O)O-aryl, OC(O)-alkyl, OC(O)-aryl, $C(O)NH_2$, C(O)NH-alkyl, C(O)NH-aryl, NHCHO, NHC(O)-alkyl, NHC(O)-aryl, NH-cycloalkyl and NH-heterocyclyl.

A subject of the present invention is the processes for preparing the products of formula (I).

The products according to the invention can be prepared using conventional organic chemistry methods.

Scheme 1 below is an illustration of the method used for the preparation of examples 1 and 3. In this respect, it cannot constitute a limitation to the scope of the invention, as regards the method for preparing the compounds claimed.

Scheme 1

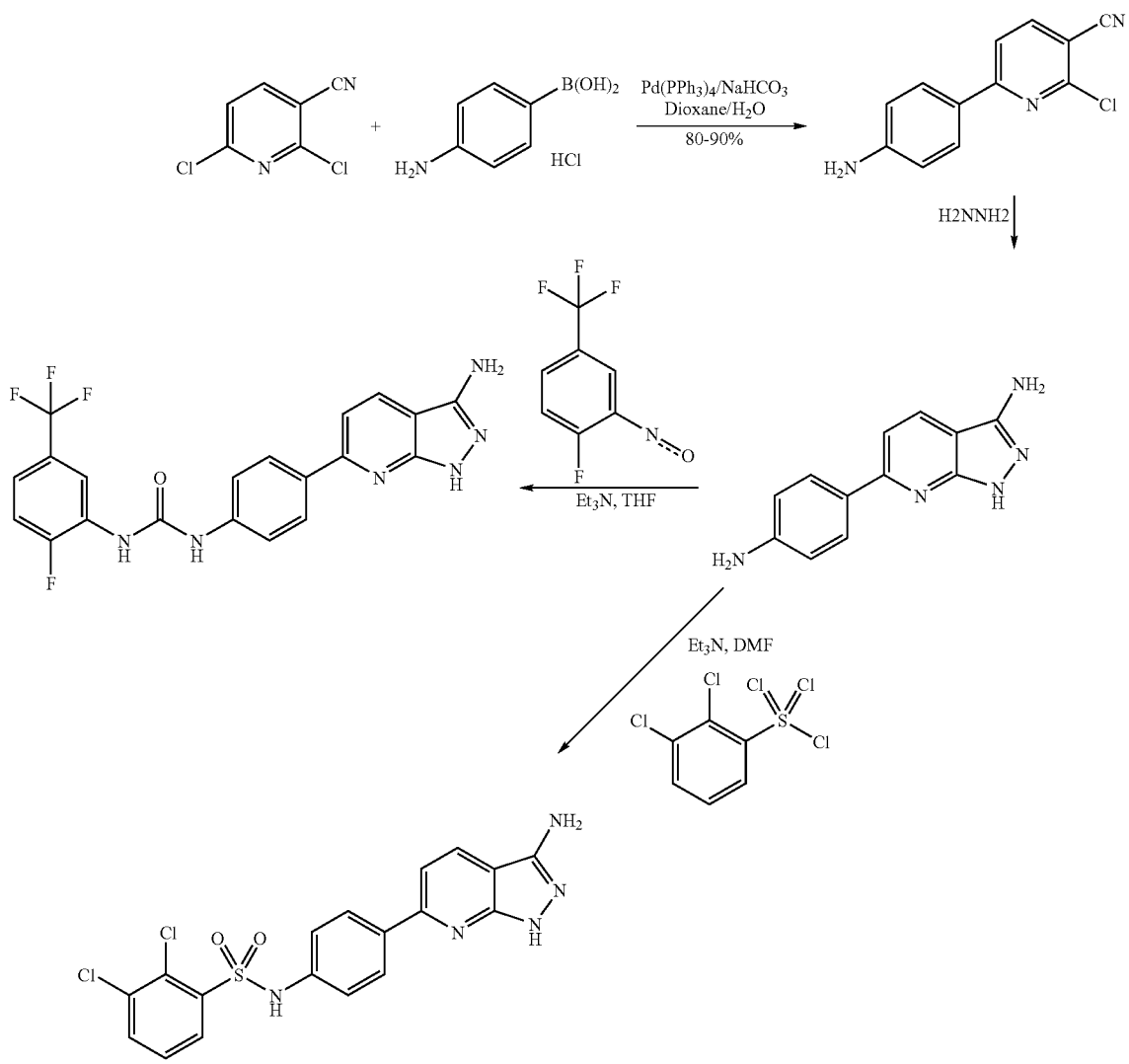

Scheme 2 below is an illustration of an alternative method used for the preparation of example 1. In this respect, it cannot constitute a limitation to the scope of the invention, as regards the methods for preparing the compounds claimed.

Scheme 2

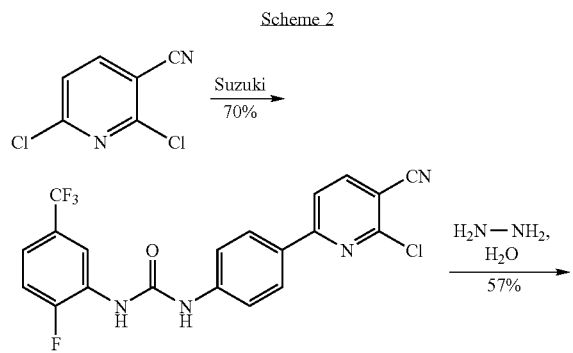

-continued

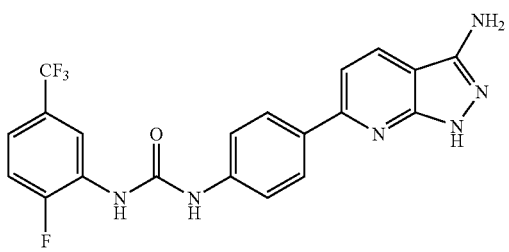

Scheme 3 below is an illustration of a method used for the preparation of examples 6 to 8, 20 to 21, 33 to 35, and 38 to 39. In this respect, it cannot constitute a limitation to the scope of the invention, as regards the methods for preparing the compounds claimed.

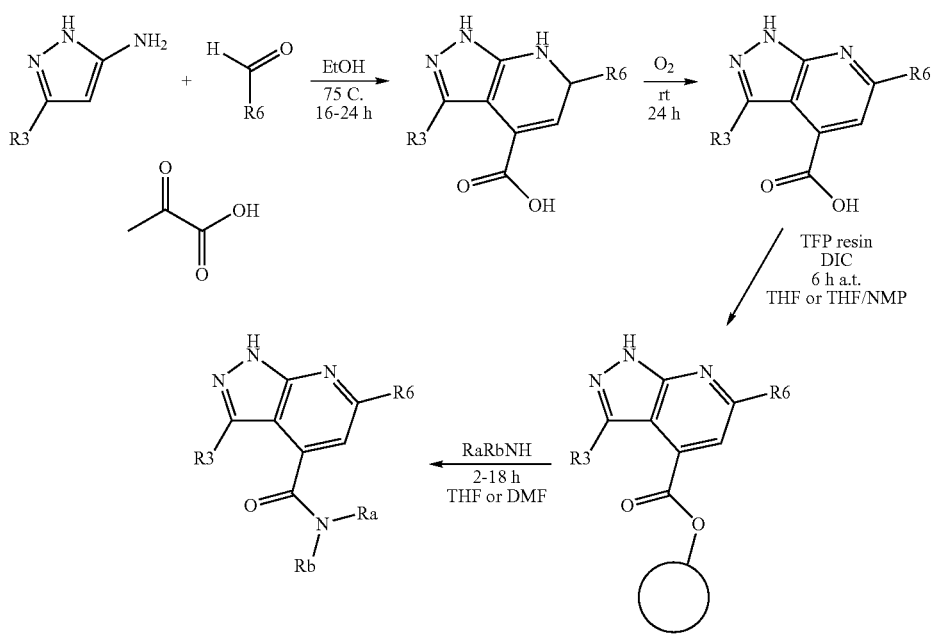
Scheme 4 below is an illustration of a method used for the preparation of examples 4, 9 to 19, 22 to 32, 36 to 37, and 44 to 62. In this respect, it cannot constitute a limitation to the scope of the invention, as regards the methods for preparing the compounds claimed.
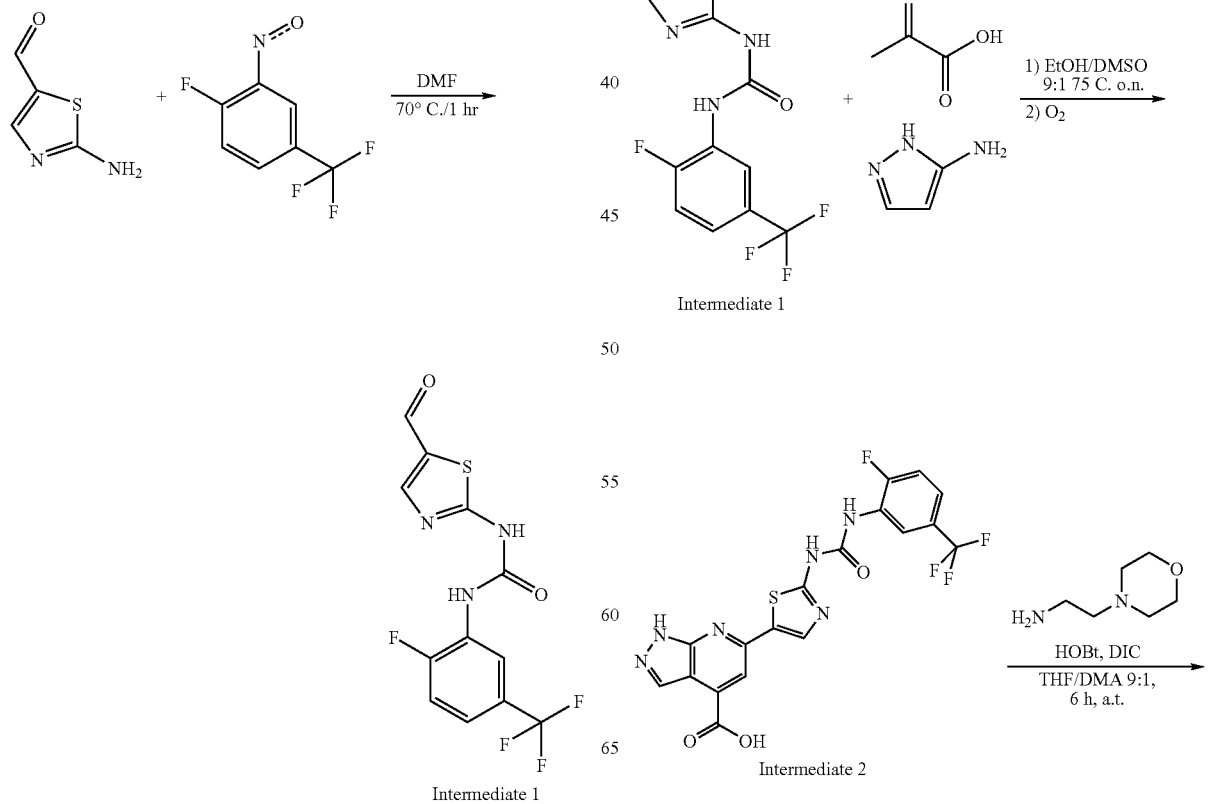

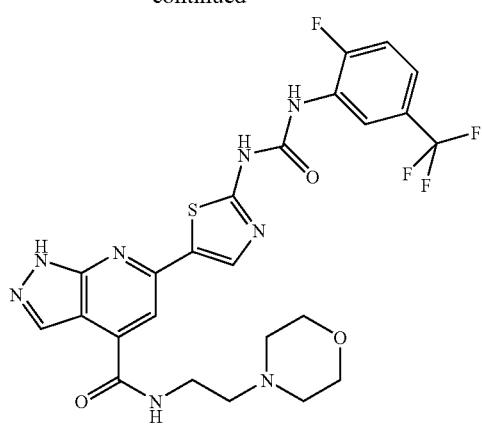
Scheme 5 below is an illustration of a method used for the preparation of examples 5, and 40 to 43. In this respect, it cannot constitute a limitation to the scope of the invention, as regards the methods for preparing the compounds claimed.
Scheme 5
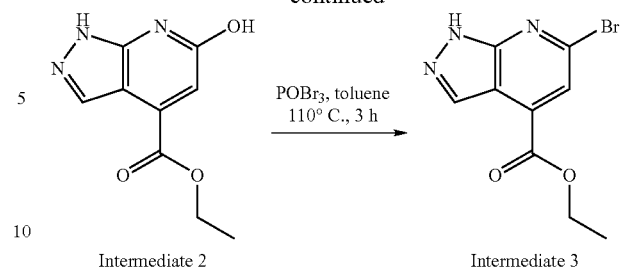
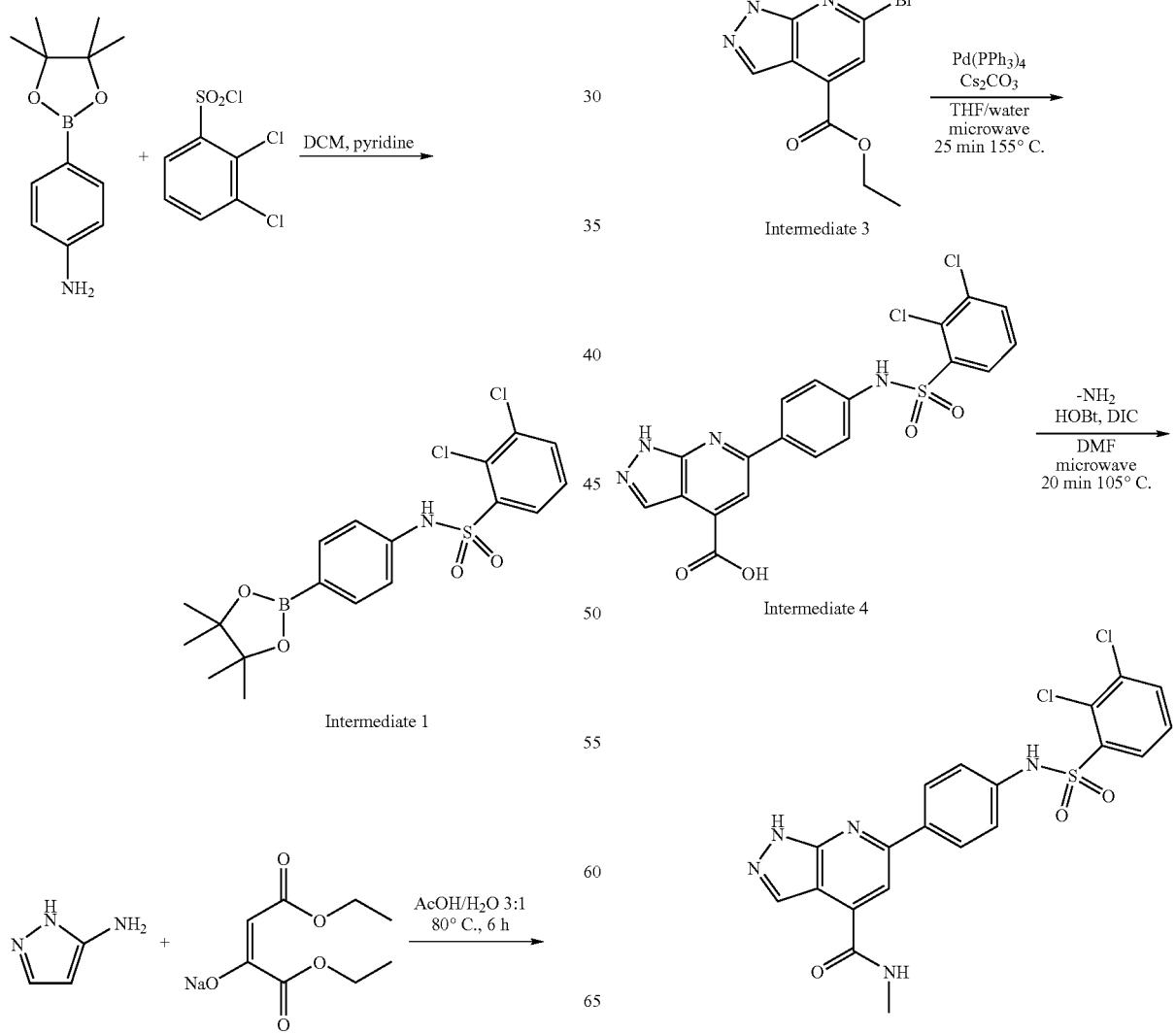

For those skilled in the art, it is understood that, in order to carry out the processes according to the invention described above, it may be necessary to introduce protective groups for amino, carboxyl and alcohol functions in order to prevent side reactions. These groups are those which are able to be removed without the rest of the molecule being affected. As examples of amino function-protecting groups, mention may be made of tert-butylcarbamate, which can be regenerated by means of trifluoroacetic acid or of iodotrimethylsilane, and acetyl which can be regenerated in an acidic medium (hydrochloric acid, for example). As carboxyl function-protecting groups, mention may be made of esters (methoxymethyl ester, benzyl ester, for example). As alcohol function-protecting groups, mention may be made of esters (benzoyl ester, for example) which can be regenerated in an acidic medium or by catalytic hydrogenation. Other protective groups which can be used are described by T. W. GREENE et al. in Protective Groups in Organic Synthesis, third edition, 1999, Wiley-Interscience.

A subject of the present invention is also the products of general formula (II) below:

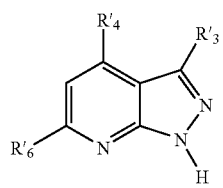

(II)

in which $R'_4$ represents R4 or H, —COOH or —COO—($C_1$-$C_6$)alkyl, $R'_3$ represents H, —$NH_2$ or —NHCO-thienyl, and $R'_6$ represents a halogen atom, an —Ar—$NH_2$ group where Ar is as defined above, or an Ar-L-A group where Ar, L and A are as defined above, and the products of the general formula (III) below:

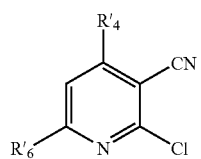

(III)

in which $R'_4$ represents R4 or H, —COOH or —COO—($C_1$-$C_6$)alkyl, and $R'_6$ represents a halogen atom, an —Ar—$NH_2$ group where Ar is as defined above, or an Ar-L-A group where Ar, L and A are as defined above. These products are in particular useful as synthesis intermediates in the processes for preparing the products of general formula (I).

The compounds of formula (I) are isolated and can be purified by the usual known methods, for example by crystallization, chromatography or extraction.

The enantiomers and diastereoisomers of the compounds of formula (I) are also part of the invention.

The compounds of formula (I) containing a basic residue can be optionally converted into addition salts with an inorganic or organic acid, by the action of such an acid in a solvent, for example an organic solvent such as an alcohol, a ketone or an ether or a chlorinated solvent.

The compounds of formula (I) containing an acidic residue can be optionally converted into metal salts or into addition salts with nitrogenous bases according to the methods known per se. These salts can be obtained by the action of a metal base (alkali metal or alkaline earth metal, for example), of ammonia, of an amine or of an amine salt on a compound of formula (I), in a solvent. The salt formed is separated by the usual methods.

These salts are also part of the invention.

When a product according to the invention has at least one free basic function, pharmaceutically acceptable salts can be prepared by reaction between said product and an inorganic or organic acid. Pharmaceutically acceptable salts include chlorides, nitrates, sulphates, hydrogen sulphates, pyrosulphates, bisulphates, sulphites, bisulphites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulphonates, p-toluenesulphonates, propanesulphonates, xylenesulphonates, salicylates, cinnamates, glutamates, aspartates, glucuronates and galacturonates.

When a product according to the invention has at least one free acid function, pharmaceutically acceptable salts can be prepared by reaction between said product and an inorganic or organic base. Pharmaceutically acceptable bases include hydroxides of cations of alkali metals or alkaline earth metals, such as Li, Na, K, Mg or Ca, and basic aminated compounds such as ammonia, arginine, histidine, piperidine, morpholine, piperazine or triethylamine.

The invention is also described by the following examples, given by way of illustration of the invention.

The LC/MS analyses were performed on an LCT Micromass machine connected to an HP 1100 device. The abundance of the products was measured using an HP G1315A diode array detector over a wavelength range of 200-600 nm and a Sedex 65 light scattering detector. The mass spectra were acquired over a range of 180 to 800. The data were analyzed using the Micromass MassLynx software. The separation was performed on a Hypersil BDS C18, 3 μm (50×4.6 mm) column, eluting with a linear gradient of 5% to 90% acetonitrile containing 0.05% (v/v) of trifluoroacetic acid (TFA) in water containing 0.05% (v/v) of TFA, over 3.5 min at a flow rate of 1 ml/min. The total analysis time, including the column reequilibration period, is 7 min.

The MS spectra were acquired in electrospray ($ES^+$) mode on a Platform II (Micromass) device. The main ions observed are described.

The melting points were measured by capillary, on a Mettler FP62 device, over the range 30° C. to 300° C., with a temperature rise of 2° C. per minute.

Purification by LC/MS:

The products may be purified by LC/MS using a Waters FractionsLynx system composed of a Waters model 600 gradient pump, a Waters model 515 regeneration pump, a Waters Reagent Manager dilution pump, a Waters model 2700 autoinjector, two Rheodyne model LabPro valves, a Waters model 996 diode array detector, a Waters model ZMD mass spectrometer and a Gilson model 204 fraction collector. The system was controlled by the Waters FractionLynx software. The separation was performed alternately on two Waters Symmetry columns ($C_{18}$, 5 μM, 19×50 mm, catalogue reference 186000210), one column undergoing regeneration with a 95/5 (v/v) water/acetonitrile mixture containing 0.07% (v/v) of trifluoroacetic acid, while the other column was being used for separation. The columns were eluted using a linear gradient of 5% to 95% of acetonitrile containing 0.07% (v/v) of trifluoroacetic acid in water containing 0.07% (v/v) of trifluoroacetic acid, at a flow rate of 10 ml/min. On leaving the separation column, one thousandth of the effluent is separated out using an LC Packing Accurate device, diluted with methanol at a flow rate of 0.5 ml/min and conveyed to the detectors, in a proportion of 75% to the diode array detector, and the remaining 25% to the mass spectrometer. The rest of the effluent (999/1000) is conveyed to the fraction collector, where the flow is discarded if the mass of the expected product is not detected by the FractionLynx software. The molecular formulae of the expected products are supplied to the FractionLynx software, which triggers the collection of the product when the mass signal detected corresponds to the $[M+H]^+$ ion and/or to the $[M+Na]^+$ ion. In certain cases, depending on the analytical LC/MS results, when an intense ion corresponding to $[M+2H]^{++}$ was detected, the value corresponding to half the calculated molecular mass (MW/2) is also supplied to the FractionLynx software. Under these conditions, collection is also triggered when the mass signal of the $[M+2H]^{++}$ and/or $[M+Na+H]^{++}$ ion is detected. The products were collected in tared glass tubes. After collection, the solvents were evaporated off, in a Savant AES 2000 or Genevac HT8 centrifugal evaporator and the masses of the products were determined by weighing the tubes after evaporation of the solvents.

EXAMPLE 1

1-[4-(3-Amino-1H-pyrazolo[3,4-b]pyridin-6-yl)phenyl]-3-(2-fluoro-5-trifluoromethylphenyl)urea

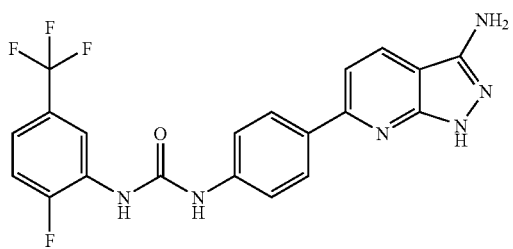

100 mg (0.44 mmol) of 6-(4-aminophenyl)-1H-pyrazolo[3,4-b]pyridin-3-ylamine are partially solubilized in 2.5 ml of anhydrous THF. The mixture is then degassed for 15 minutes with argon. 61.55 µl (44.93 mg, 0.44 mmol, 1 eq.) of triethylamine are subsequently added. The solution is once again degassed for 15 minutes. Finally, 64.22 µl (91 mg, 0.44 mmol, 1 eq.) of 2-fluoro-5-(trifluoromethyl)phenyl isocyanate are added dropwise. The mixture is stirred for 2 hours at ambient temperature under an inert atmosphere. After reaction, the mixture is filtered. The filtrate is concentrated. A beige solid is isolated. This crude product is subsequently purified on a C18 reverse-phase silica (13 g) column with an eluent gradient of 5% to 95% of acetonitrile in water. The fractions containing the expected product are lyophilized. A white solid is isolated (10 mg).

MS (ES) MH$^+$ m/z=431.

$^1$H NMR (DMSO-d6) d 5.52 (broad s, 2H); 7.39 (m, 1H); 7.49 (m partially masked, 1H); 7.52 (d, J=8.5 Hz, 1H); 7.62 (broad d, J=8.5 Hz, 2H); 8.07 (broad d, J=8.5 Hz, 2H); 8.13 (d, J=8.5 Hz, 1H); 8.60 (broad d, J=7.5 Hz, 1H); 9.21 (broad m, 1H); 9.63 (broad m, 1H); 11.9 (broad m, 1H).

6-(4-Aminophenyl)-1H-pyrazolo[3,4-b]pyridin-3-ylamine

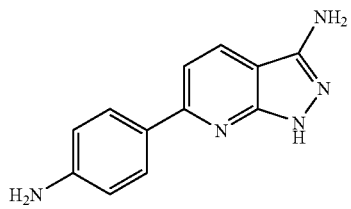

In an appropriately sized microwave reactor, 0.97 mmol (222 mg) of 6-(4-aminophenyl)-2-chloronicotinonitrile is suspended in 3.3 ml of 1-propanol. 0.28 ml (0.290 g, 5.80 mmol, 6 eq.) of hydrazine hydrate is added. The suspension is heated for 45 minutes at 130° C. in a microwave oven. The mixture is filtered and the solid is dried so as to obtain a green solid (215 mg).

MS (EI) M$^+$ m/z=225.

$^1$H NMR (DMSO-d6) d 5.41 (sl, 4H), 6.63 (d, J=8 Hz, 2H), 7.37 (d, J=8 Hz, 1H), 7.82 (d, J=8 Hz, 2H), 8.02 (d, J=2 Hz, 1H).

6-(4-Aminophenyl)-2-chloronicotinonitrile

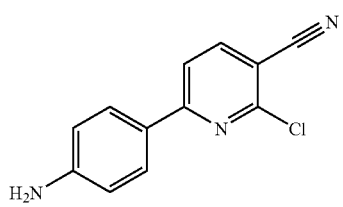

2.89 mmol (500 mg) of 2,6-dichloronicotinonitrile and 3.18 mmol (551 mg, 1.1 eq.) of 4-aminophenylboronic acid are dissolved under an inert atmosphere in 33.3 ml of dioxane. 680 mg (8.09 mmol, 2.8 eq.) of sodium bicarbonate and then 8.3 ml of water are subsequently added. The mixture is stirred for 5 minutes under an inert atmosphere and then 334 mg (0.29 mmol, 0.1 eq.) of tetrakis(triphenylphosphine)palladium are added. The reaction mixture is brought to reflux (100° C.) for 2 hours and is then cooled to ambient temperature. The reaction medium is filtered and then extracted four times with ethyl acetate. The organic phases are combined, washed twice with a saturated aqueous sodium chloride solution, dried with magnesium sulphate, and concentrated. A yellow solid is then obtained. This crude is purified on a column of 90 g of silica, with an eluent gradient of 20% to 50% of ethyl acetate in heptane. The expected product is obtained in the form of a yellow solid (531 mg).

MS (ES) MH$^+$ m/z=230.

$^1$H NMR (DMSO-d6) d 5.94 (sl, 2H), 6.65 (d, j=8 hz, 2H), 7.89 (d, j=8 hz, 2H), 7.93 (d, j=8 hz, 1H), 8.27 (d, j=8 hz, 1H).

Alternative pathway for the preparation of 1-[4-(3-amino-1H-pyrazolo[3,4-b]pyridin-6-yl)phenyl]-3-(2-fluoro-5-trifluoromethylphenyl)urea (scheme 2):

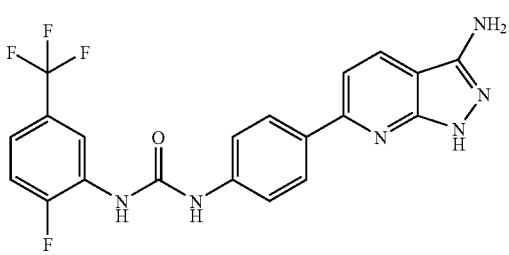

0.46 mmol (200 mg) of 1-[4-(6-chloro-5-cyanopyridin-2-yl)phenyl]-3-(2-fluoro-5-trifluoromethylphenyl)urea is suspended in 3.2 ml of 1-propanol. 0.13 ml (0.14 g, 2.76 mmol, 6 eq.) of hydrazine hydrate is added. The suspension is heated at 80° C. for 10 h. The mixture is filtered and the solid is dried so as to obtain 140 mg of the expected product.

1-[4-(6-Chloro-5-cyanopyridin-2-yl)phenyl]-3-(2-fluoro-5-trifluoromethylphenyl)urea

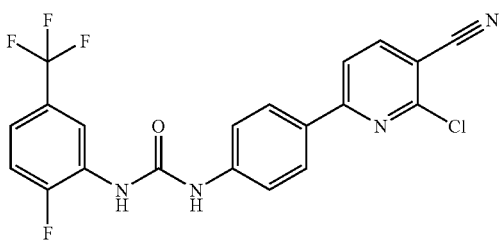

0.578 mmol (100 mg) of 2,6-dichloronicotinonitrile and 0.64 mmol (270 mg, 1.1 eq.) of 1-(2-fluoro-5-trifluoromethylphenyl)-3-[4-(4,4,5,5-tetramethyl[1,3,2]dioxaborolan-2-yl)phenyl]urea are dissolved under an inert atmosphere in 6.6 ml of dioxane. 136 mg (1.62 mmol, 2.8 eq.) of sodium bicarbonate and then 1.6 ml of water are subsequently added. The mixture is stirred for 5 minutes under an inert atmosphere and then 33.4 mg (0.029 mmol, 0.05 eq.) of tetrakis(triphenylphosphine)palladium are added. The mixture is refluxed (100° C.) for 2 hours and is then cooled to ambient temperature. The reaction medium is extracted twice with ethyl acetate. The organic phases are combined, washed twice with a saturated aqueous sodium chloride solution, and then dried with magnesium sulphate and concentrated. A yellow solid is then obtained. The crude is purified on a column of 30 g of silica, with an eluent gradient of 20% to 40% of ethyl acetate in heptane. A yellow solid is obtained (175 mg).

MS (ES) MH$^+$ m/z=435.

$^1$H NMR (DMSO-d6) d 7.40 (m, 1H), 7.49 (m, 1H), 7.68 (d, J=8 Hz, 2H), 8.13 (d, J=8 Hz, 2H), 8.16 (d, J=8 Hz, 1H), 8.45 (d, J=8 Hz, 1H), 8.56 (m, 1H).

The 1-(2-fluoro-5-trifluoromethylphenyl)-3-[4-(4,4,5,5-tetramethyl[1,3,2]dioxaborolan-2-yl)phenyl]urea is prepared according to the following procedure:

936 mg of 2-fluoro-5-trifluoromethylphenylisocyanate and then 0.64 ml of triethylamine are added to a solution of 1 g of 4-(4,4,5,5-tetramethyl[1,3,2]dioxaborolan-2-yl)aniline in 15 ml of tetrahydrofuran, at ambient temperature. The reaction medium is stirred at ambient temperature for 18 h, and then treated with methanol and then, finally, evaporated to dryness under reduced pressure. The residue thus obtained is purified by chromatography on silica using, as eluent, a (99.5/0.5 then 90/10) methylene chloride/methanol mixture. The fractions containing the expected product are concentrated to dryness so as to give 1.45 g of 1-(2-fluoro-5-trifluoromethylphenyl)-3-[4-(4,4,5,5-tetramethyl[1,3,2]dioxaborolan-2-yl)phenyl]urea in the form of a white solid. MS (ES) MH$^+$ m/z=425.

EXAMPLE 2

Thiophene-3-carboxylic acid (6-{4-[3-(2-fluoro-5-trifluoromethylphenyl)ureido]phenyl}-1H-pyrazolo[3,4-b]pyridin-3-yl)amide

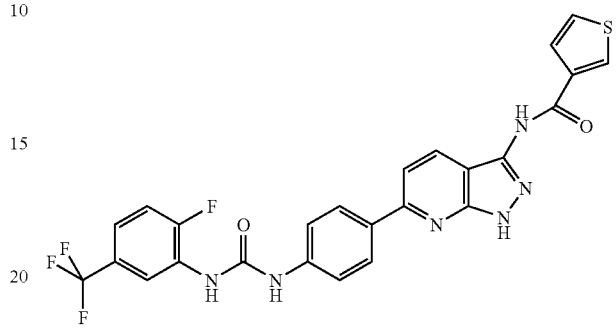

A solution of 1-[4-(3-amino-1H-pyrazolo[3,4-b]pyridin-6-yl)phenyl]-3-(2-fluoro-5-trifluoromethylphenyl)urea (80.0 mg, 0.186 mmol) in pyridine (2 ml) is cooled to 5° C. under argon and thiophene-3-carboxylic acid chloride (27 mg, 0.186 mmol, 1.0 eq.) is added. The mixture is stirred at ambient temperature for 5.5 h. Another equivalent of thiophene-3-carboxylic acid chloride (27 mg, 0.186 mmol) is added and the mixture is stirred at ambient temperature overnight. The reaction is taken up with water, and then extracted with ethyl acetate. The organic phase is washed twice with a salt solution, dried with magnesium sulphate, and concentrated. An orange yellow solid is then obtained. The crude is purified on a silica column, with an eluent gradient of 0% to 5% of methanol in dichloromethane. A beige solid is obtained:

13.5 mg.

MS (ES) MH$^+$ m/z=541

$^1$H NMR (DMSO-d6) d 7.40 (m, 1H); 7.50 (m, 1H); 7.65 (broad d, J=9.0 Hz, 2H); 7.68 (dd partially masked, J=3.0 and 5.0 Hz, 1H); from 7.71 to 7.75 (m, 2H); 8.15 (broad d, J=9.0 Hz, 2H); 8.39 (d, J=8.5 Hz, 1H); 8.50 (broad d, J=3.0 Hz, 1H); 8.61 (dd, J=2.5 and 7.5 Hz, 1H); 9.21 (broad m, 1H); 9.67 (broad m, 1H); 10.9 (broad m, 1H); 13.3 (broad m, 1H).

EXAMPLE 3

N-[4-(3-Amino-1H-pyrazolo[3,4-b]pyridin-6-yl)phenyl]-2,3-dichlorobenzenesulphonamide

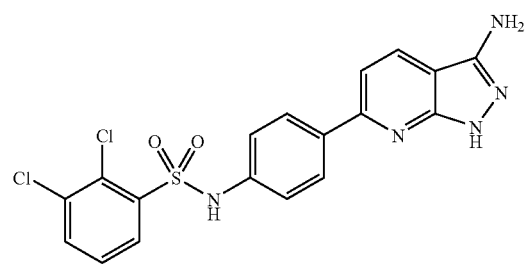

100 mg (0.44 mmol) of 6-(4-aminophenyl)-1H-pyrazolo[3,4-b]pyridin-3-ylamine are dissolved in 3 ml of anhydrous DMF. The solution is then degassed for 15 minutes with argon. 123.8 μl (89.9 mg, 0.89 mmol, 2 eq.) of triethylamine are subsequently added. The solution is once again degassed for 15 minutes. Finally, 0.109 g (0.444 mmol, 1 eq.) of 2,3-dichlorophenylsulphonyl chloride is added. The solution is stirred at ambient temperature under argon overnight. At the end of the reaction, 10 ml of water are added. A yellow-brown precipitate forms. The mixture is filtered. The solid is dried and purified on a column of 4 g of silica with an eluent gradient of 0 to 10% of methanol in dichloromethane. A beige solid is isolated (11 mg).

MS (ES) MH+ m/z=434.

$^1$H NMR (DMSO-d6, 373K) d 5.09 (broad s, 2H); 7.09 (broad d, J=8.5 Hz, 2H); 7.37 (d, J=8.5 Hz, 1H); 7.40 (broad t, J=8.5 Hz, 1H); 7.69 (broad d, J=8.5 Hz, 1H); 7.85 (broad d, J=8.5 Hz, 2H); 8.02 (broad d, J=8.5 Hz, 1H); 8.06 (d, J=8.5 Hz, 1H); 11.5 (broad m, 1H).

EXAMPLE 4

6-{2-[3-(2-Fluoro-5-trifluoromethyl phenyl)ureido]thiazol-5-yl}-1H-pyrazolo[3,4-b]pyridine-4-carboxylic acid (2-morpholin-4-ylethyl)amide trifluoroacetate

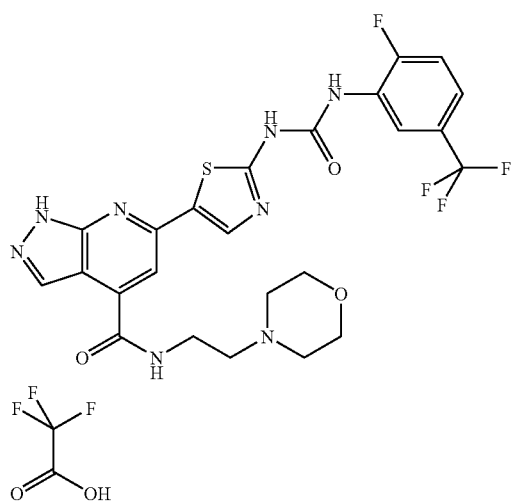

The product of example 4 can be prepared by the process described above in scheme 4:

Synthesis of Intermediate 1:

2-Fluoro-(5-trifluoromethyl)phenylisocyanate (4 g, 19.5 mmol) is added to a solution of 2-aminothiazole-5-carboxaldehyde (2.5 g, 19.5 mmol) in DMF (120 ml). The solution is heated at 70° C. for 1 h, evaporated, and purified by chromatography on silica gel, eluting with 1:1 hexane/EtOAc. The fractions containing intermediate 1 are combined and evaporated so as to provide intermediate 1 in the form of a yellow solid (4.28 g).

Synthesis of Intermediate 2:

Added to a solution of intermediate 1 (88 mg, 0.26 mmol) in a 9:1 ethanol/DMSO mixture (2 ml) is a solution of 1H-pyrazol-3-ylamine (22 mg, 0.26 mmol) in 2 ml of the same mixture of solvents containing pyruvic acid (23 mg, 0.26 mmol). The mixture is heated at 75° C. for 24 h in the presence of oxygen, and the reaction medium is then evaporated to dryness so as to provide intermediate 2 in the form of an orange solid which is used as it is in the subsequent step.

Preparation of the Product of Example 4

Intermediate 2 is dissolved in dry THF (2 ml) and HOBt (36 mg, 0.26 mmol) then DIC is added (42 μl, 0.26 mmol). After 5 min, 2-morpholin-4-ylethylamine (39 μl, 0.3 mmol) is added. The stirring is continued for 5 h at ambient temperature, and the reaction medium is then evaporated under reduced pressure. The residue is purified by chromatography on silica gel, eluting with 94:5:1 EtOAc/MeOH/TEA using a gradient of 90:9:1 EtOAc/MeOH/TEA. The fractions containing the product are combined and evaporated, and then purified by LC/MS chromatography (reverse-phase, eluent water+0.1% TFA with a gradient of 25% to 85% of acetonitrile over a period of 8 minutes). The fractions containing the expected product are combined and evaporated under reduced pressure so as to provide the product in the form of a yellow solid (10.6 mg).

EXAMPLE 5

N-[4-(3-Amino-4-methylaminocarbonyl-1H-pyrazolo[3,4-b]pyridin-6-yl)phenyl]-2,3-dichlorobenzenesulphonamide

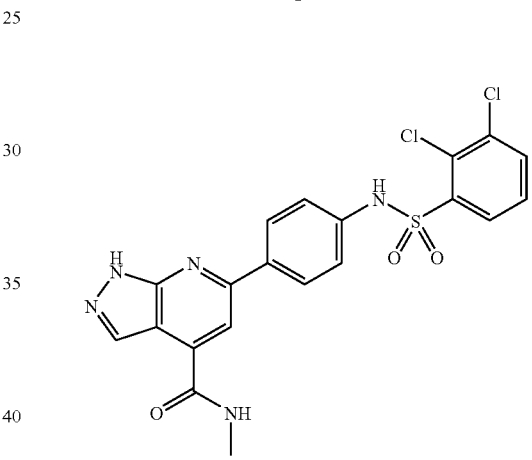

The product of example 5 can be prepared by means of the process described above in scheme 5:

Synthesis of Intermediate 1

219 mg of 4-(4,4,5,5-tetramethyl-1,3,2-dioxaborolan-2-yl)aniline are dissolved with 245 mg (1 mmol) of 2,3-dichlorobenzenesulphonyl chloride in 2 ml of DCM and 120 μl (1.5 μmol) of pyridine. The mixture is stirred for 6 hours at ambient temperature and then dried under vacuum so as to obtain the desired product in the form of a light red solid.

MS (ES) MH+ m/z=428.

Synthesis of Intermediate 2

84 g of diethyl oxalacetate sodium salt are dissolved with 33.2 g of 2-aminopyrazole in 600 ml of AcOH/H$_2$O (1:3). The mixture is heated for 6 hours at 80° C. The product is precipitated after cooling, filtered, and dried under vacuum (17.9 g).

$^1$H NMR (600 MHz, DMSO-d6) δppm: 13.74 (s, 1H), 12.39 (s, 1H), 8.22 (s, 1H), 6.70 (s, 1H), 4.40 (q, J=7.1 Hz) 2H), 1.40 (t, J=7.1 Hz) 3H).

Synthesis of Intermediate 3:

2.07 g (10 mmol) of intermediate 2, 20 ml of toluene and 2.87 g (10 mmol) of POBr$_3$ are heated in an oil bath to 110° C., with stirring. The mixture is evaporated and purified on a column of silica, eluted with 20% EtOAc, 80% hexane, so as to give (after evaporation) 300 mg of the desired product.

¹H NMR (600 MHz, DMSO-d6) δppm: 14.45 (s, 1H), 8.41 (s, 1H), 7.79 (s, 1H), 4.49 (q, J=7.1 Hz) 2H), 1.46 (t, J=7.1 Hz) 3H).

Synthesis of Intermediate 4:

74 μmol of intermediate 3 (20 mg), 74 μmol of intermediate 1, 185 μmol of cesium carbonate and 7.4 μmol of Pd (PPh$_3$)$_4$ are dissolved in THF and 20% H$_2$O (total volume 750 μl). The mixture is heated in a microwave for 25 min at 155° C. (power 55 W). The product is evaporated and purified by LC/MS chromatography in water with 0.1% of trifluoroacetic acid and a gradient of 25% to 95% acetonitrile, over 9 minutes. The product is dried under vacuum. MS (ES) MH$^+$ m/z=463.

Preparation of the Product of Example 5

Intermediate 4 (20 mg, 43.3 μmol) is dissolved in DMF (0.5 ml), with HOBt (14.6 mg, 108.25 μmol) and DIC (16.9 μl, 108.25 μmol). 0.5 mmol of methylamine (1M in THF, 0.5 ml) is added. The mixture is heated in a microwave for 20 min at 105° C. (power 25 W). The product is evaporated and purified by LC/MS chromatography in water with 0.1% of trifluoroacetic acid and a gradient of 25% to 95% acetonitrile, over 9 minutes. The product is dried under vacuum so as to obtain a light yellow solid.

MS (ES) MH$^+$ m/z=476.

¹H NMR (600 MHz, DMSO-d6) δppm: 13.79 (s, 1H), 11.13 (s, 1H), 8.35 (s, 1H), 8.02 (s, 1H), 8.13 (d, J=7.8 Hz) 2H) 8.09 (d, J=8.27 Hz) 1H), 7.94 (d, J=8.05 Hz) 1H), 7.28 (d, J=4.31 Hz) 2H), 2.88 (d, J=4.31 Hz) 3H) 7.58 (q, J=8.08 Hz) 1H), 8.86 (t, J=4.43 Hz) 1H)

EXAMPLES 6 TO 62

By carrying out the procedures described above, the products of table 1 below are obtained:

| Example | Formula | ESI (MS) (m/z) |
|---|---|---|
| 6 | | 459 |
| 7 | | 473 |
| 8 | | 573 |

-continued
| Example | Formula | ESI (MS) (m/z) |
| --- | --- | --- |
| 9 | 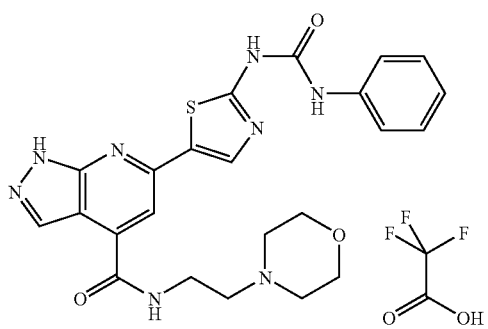 | 494 |
| 10 | 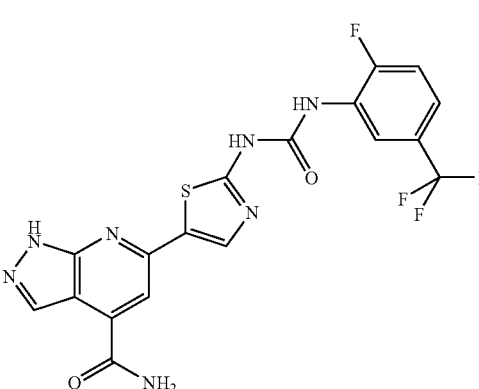 | 466 |
| 11 | 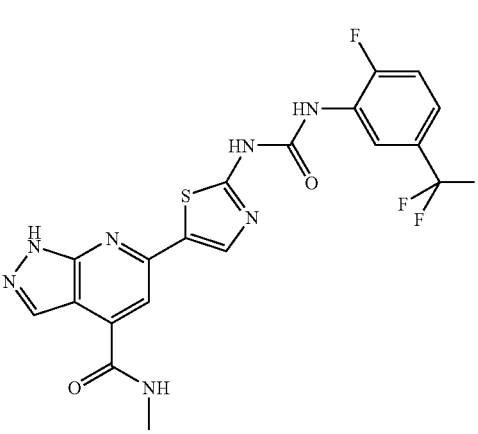 | 480 |
| 12 | 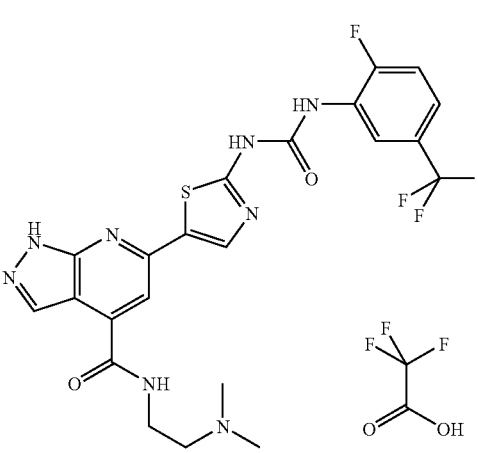 | 538 |

-continued
| Example | Formula | ESI (MS) (m/z) |
|---|---|---|
| 13 | 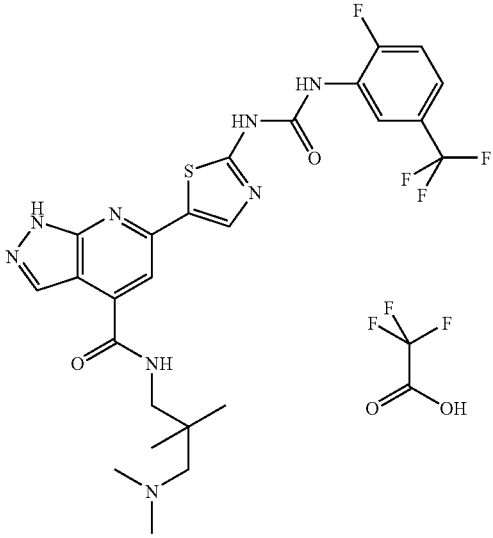 | 580 |
| 14 | 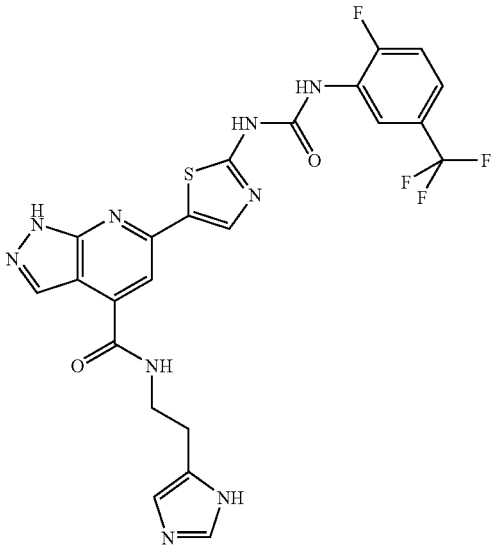 | 561 |
| 15 | 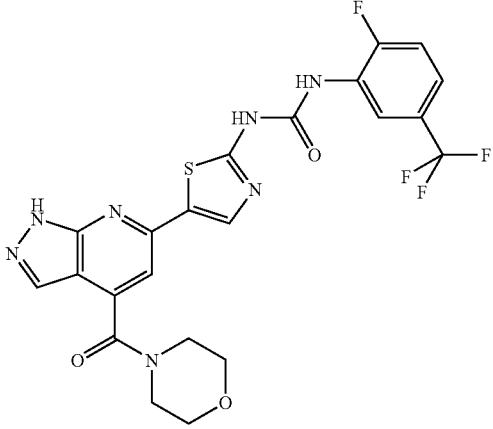 | 536 |

-continued
| Example | Formula | ESI (MS) (m/z) |
|---------|---------|----------------|
| 16 | 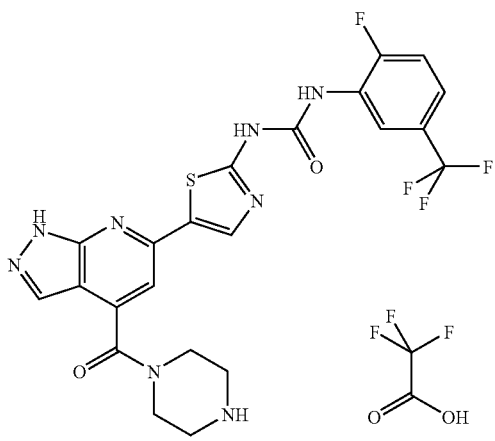 | 535 |
| 17 | 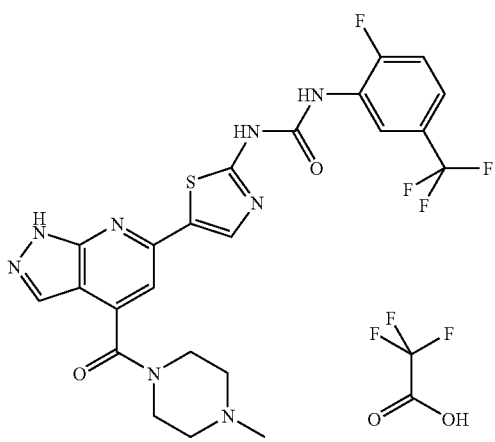 | 550 |
| 18 | 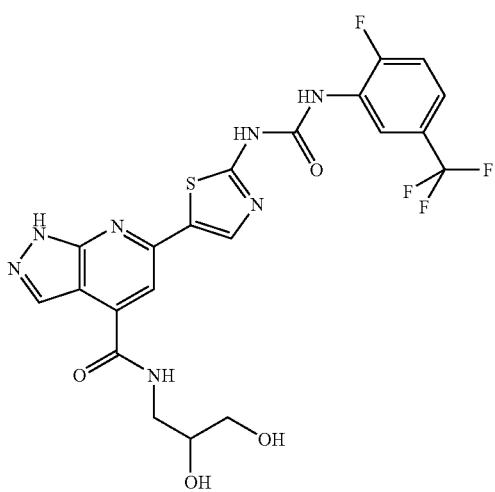 | 540 |

-continued
| Example | Formula | ESI (MS) (m/z) |
|---|---|---|
| 19 | 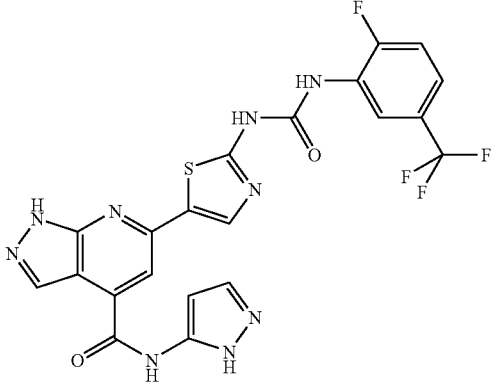 | 532 |
| 20 | 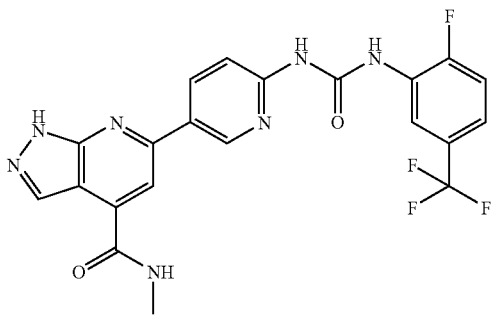 | 474 |
| 21 | 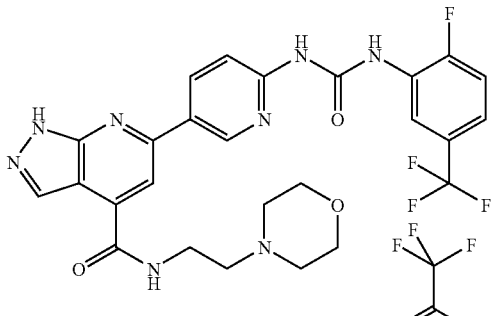 | 574 |
| 22 | 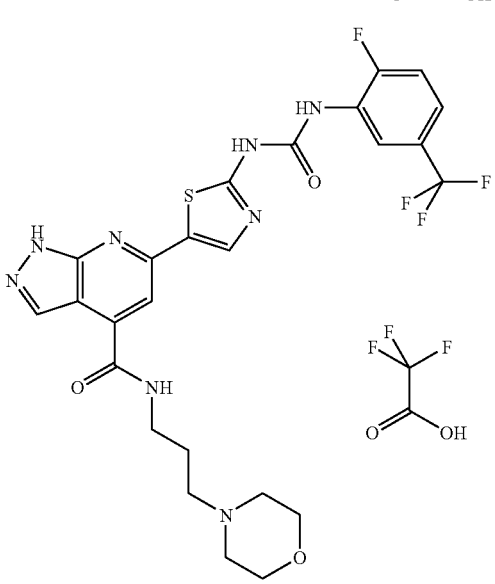 | 594 |

| Example | Formula | ESI (MS) (m/z) |
|---|---|---|
| 23 | 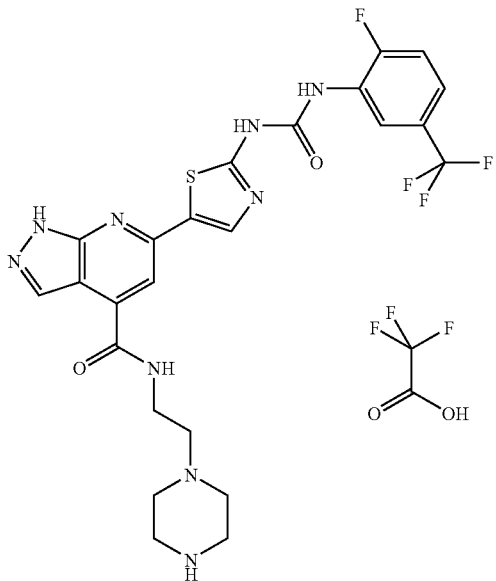 | 579 |
| 24 | 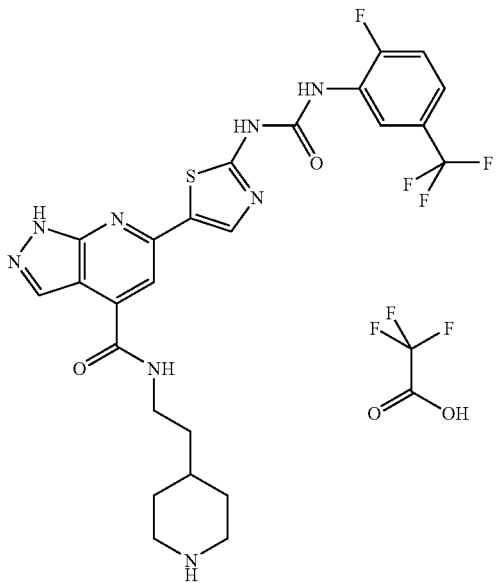 | 578 |

| Example | Formula | ESI (MS) (m/z) |
|---|---|---|
| 25 | 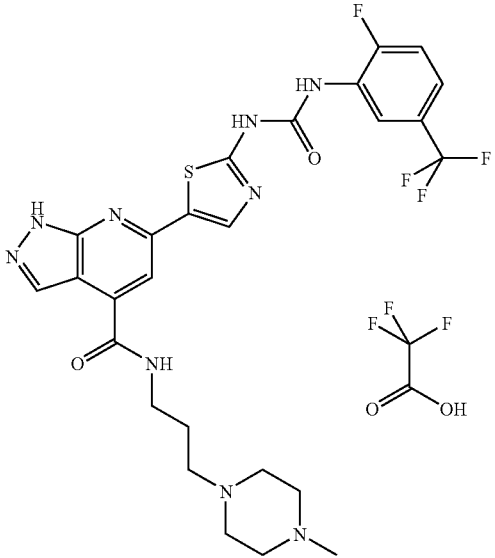 | 607 |
| 26 | 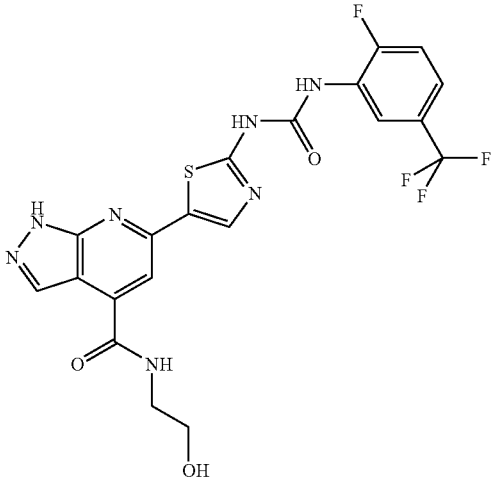 | 510 |
| 27 | 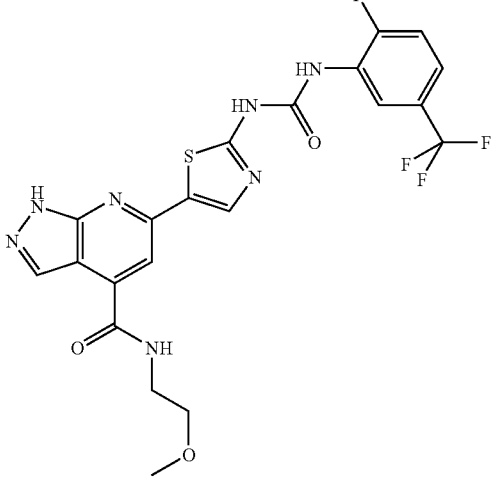 | 524 |

-continued

| Example | Formula | ESI (MS) (m/z) |
|---|---|---|
| 28 | | 558 |
| 29 | | 558 |
| 30 | | 551 |

-continued

| Example | Formula | ESI (MS) (m/z) |
|---|---|---|
| 31 | | 608 |
| 32 | | 566 |
| 33 | | 473 |
| 34 | | 573 |

| Example | Formula | ESI (MS) (m/z) |
|---|---|---|
| 35 | 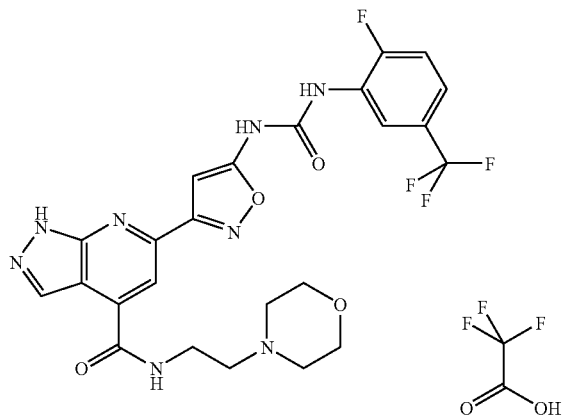 | 563 |
| 36 | 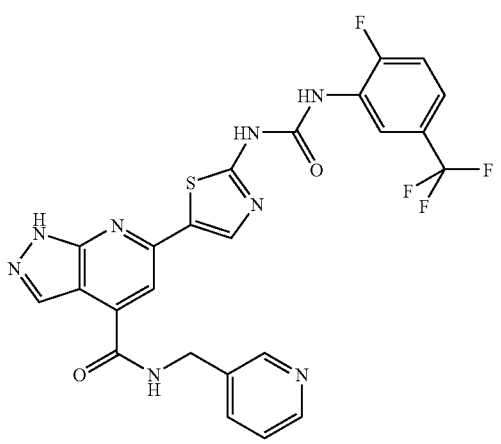 | 558 |
| 37 | 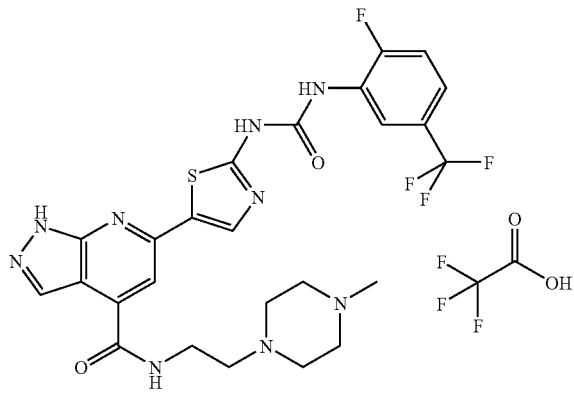 | 591 |

-continued

| Example | Formula | ESI (MS) (m/z) |
|---|---|---|
| 38 | | 581 |
| 39 | | 579 |
| 40 | | 542 |
| 41 | | 532 |

| Example | Formula | ESI (MS) (m/z) |
|---|---|---|
| 42 | 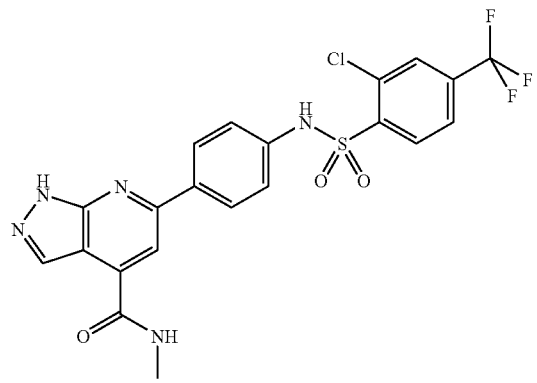 | 511 |
| 43 | 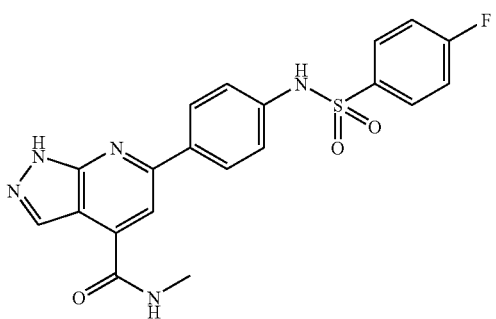 | 426 |
| 44 | 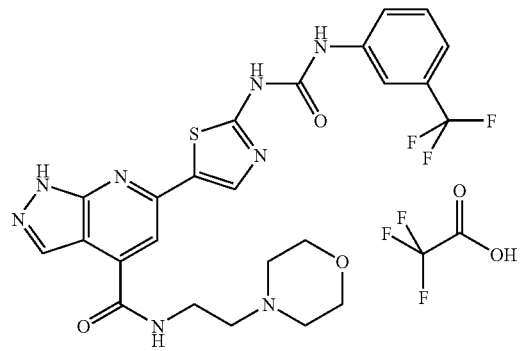 | 561 |
| 45 | 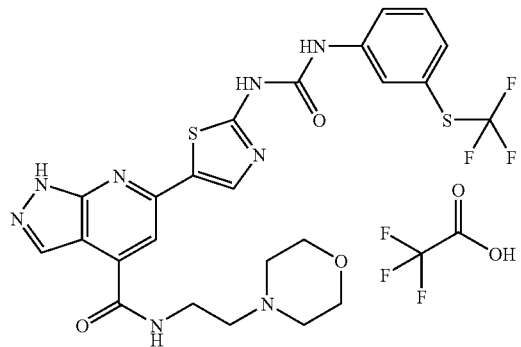 | 593 |

-continued

| Example | Formula | ESI (MS) (m/z) |
| --- | --- | --- |
| 46 | | 579 |
| 47 | | 579 |
| 48 | | 527 |

-continued

| Example | Formula | ESI (MS) (m/z) |
|---------|---------|----------------|
| 49 | | 527 |
| 50 | | 579 |
| 51 | | 545 |
| 52 | | 523 |

| Example | Formula | ESI (MS) (m/z) |
|---|---|---|
| 53 | 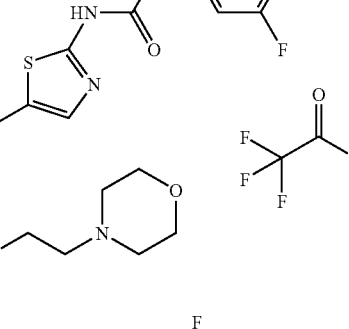 | 529 |
| 54 | 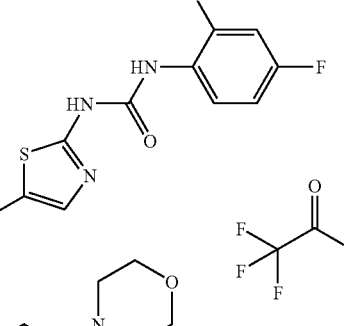 | 529 |
| 55 | 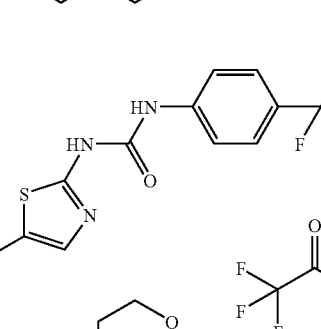 | 561 |
| 56 | 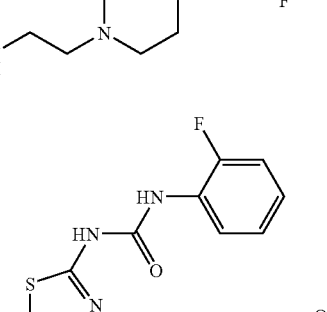 | 511 |

| Example | Formula | ESI (MS) (m/z) |
|---|---|---|
| 57 | (structure) | 561 |
| 58 | (structure) | 577 |
| 59 | (structure) | 518 |
| 60 | (structure) | 523 |

-continued

| Example | Formula | ESI (MS) (m/z) |
|---|---|---|
| 61 | 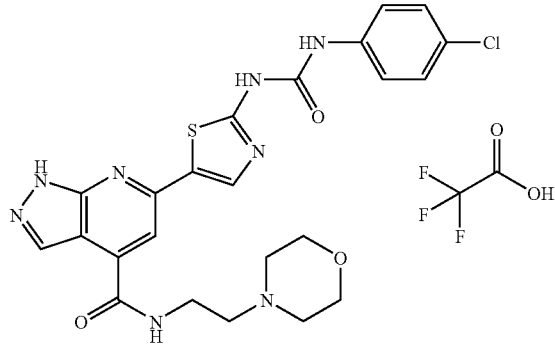 | 527 |
| 62 | 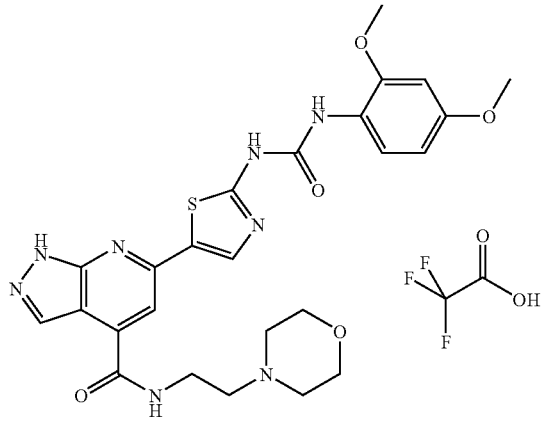 | 553 |

Determination of the Activity of the Compounds—Experimental Protocols

1. FAK

The inhibitory activity of the compounds on FAK is determined by measuring the inhibition of autophosphorylation of the enzyme using a time resolved fluorescence assay (HTRF).

The complete cDNA of human FAK, the N-terminal end of which had been labelled with histidine, was cloned into a baculovirus expression vector pFastBac HTc. The protein was expressed and purified to approximately 70% homogeneity.

The kinase activity is determined by incubating the enzyme (6.6 μg/ml) with various concentrations of test compound in a 50 mM Hepes buffer, pH=7.2, containing 10 mM $MgCl_2$, 100 μM $Na_3VO_4$, and 15 μM of ATP for 1 hour at 37° C. The enzymatic reaction is stopped by the addition of Hepes buffer, pH=7.0, containing 0.4 mM KF, 133 mM EDTA and 0.1% BSA and the labelling is carried out, for 1 to 2 hours at ambient temperature, by the addition, to this buffer, of an anti-histidine antibody labelled with XL665 and of a tyrosine phospho-specific monoclonal antibody conjugated to europium cryptate (Eu-K). The characteristics of the two fluorophores are available in G. Mathis et al., Anticancer Research, 1997, 17, pages 3011-3014. The transfer of energy from the excited europium cryptate to the acceptor XL665 is proportional to the degree of autophosphorylation of FAK. The XL-665-specific long-lasting signal is measured in a Packard Discovery plate counter. All the assays were carried out in duplicate and the mean of the two assays is calculated. The inhibition of the FAK autophosphorylation activity with compounds of the invention is expressed as percentage inhibition relative to a control, the activity of which is measured in the absence of test compound. For calculating the % inhibition, the [signal at 665 nm/signal at 620 nm] ratio is considered.

2. KDR

The inhibitory effect of the compounds is determined in an assay of substrate phosphorylation by the KDR enzyme in vitro using a scintillation technique (96-well plate, NEN).

The cytoplasmic domain of the human KDR enzyme was cloned in the form of a GST fusion into the baculovirus expression vector pFastBac. The protein was expressed in SF21 cells and purified to approximately 60% homogeneity.

The kinase activity of KDR is measured in 20 mM MOPS, 10 mM $MgCl_2$, 10 mM $MnCl_2$, 1 mM DTT, 2.5 mM EGTA and 10 mM b-glycerophosphate, pH=7.2, in the presence of 10 mM $MgCl_2$, 100 μM $Na_3VO_4$ and 1 mM NaF. 10 μl of the compound are added to 70 μl of kinase buffer containing 100 ng of KDR enzyme at 4° C. The reaction is initiated by adding 20 μl of solution containing 2 μg of substrate (SH2-SH3 fragment of PLCγ expressed in the form of a GST fusion protein), 2 μCi γ$^{33}$P[ATP] and 2 μM cold ATP. After incubation for 1 hour at 37° C., the reaction is stopped by adding 1 volume (100 μl) of 200 mM EDTA. The incubation buffer is removed, and the wells are washed three times with 300 μl of PBS. The radioactivity is measured in each well using a Top Count NXT radioactivity counter (Packard).

The background noise is determined by measuring the radioactivity in four different wells containing radioactive ATP and the substrate alone.

A total activity control is measured in four different wells containing all the reactants (γ$^{33}$P-[ATP], KDR and PLCγ substrate) but in the absence of compound.

The inhibition of the KDR activity with the compound of the invention is expressed as percentage inhibition of the control activity determined in the absence of compound.

The compound SU5614 (Calbiochem) (1 µM) is included in each plate as an inhibition control.

3. Tie2

The human Tie2 coding sequence corresponding to the intracellular domain amino acids 776-1124 was generated by PCR using the cDNA isolated from human placenta as model. This sequence was introduced into a baculovirus expression vector pFastBacGT in the form of a GST fusion protein.

The inhibitory effect of the molecules is determined in an assay of PLC phosphorylation by Tie2 in the presence of GST-Tie2 purified to approximately 80% of homogeneity. The substrate is composed of the SH2-SH3 fragments of PLC expressed in the form of a GST fusion protein.

The kinase activity of Tie2 is measured in a 20 mM MOPS buffer, pH 7.2, containing 10 mM $MgCl_2$, 10 mM $MnCl_2$, 1 mM DTT and 10 mM of glycerophosphate. In a FlashPlate 96-well plate kept on ice, a reaction mixture composed of 70 µl of kinase buffer containing 100 ng of GST-Tie2 enzyme is deposited per well. 10 µl of the test molecule diluted, in DMSO, to a concentration of at most 10% are subsequently added. For a given concentration, each measurement is carried out in quadruplicate. The reaction is initiated by adding 20 µl of solution containing 2 µg of GST-PLC, 2 µM of cold ATP and 1 µCi of $^{33}P[ATP]$. After incubation for 1 hour at 37° C., the reaction is stopped by adding 1 volume (100 µl) of EDTA at 200 mM. After removal of the incubation buffer, the wells are washed three times with 300 µl of PBS. The radio-activity is measured on a Wallac MicroBeta1450.

The inhibition of the Tie2 activity is calculated and expressed as percentage inhibition relative to the control activity determined in the absence of compound.

| Example | IC 50 (nM) | | |
| --- | --- | --- | --- |
| | KDR | Tie2 | FAK |
| 1 | 119 | 192 | 10 000 |
| 2 | 6 | 7 | |
| 3 | 10 000 | 75 | 10 000 |
| 4 | 83 | 1 | 343 |
| 5 | 10 000 | 13 | 10 000 |
| 9 | 6824 | 443 | 10 000 |
| 11 | 581 | 8 | 927 |
| 12 | 2360 | 30 | |
| 13 | 373 | 4 | |
| 14 | 293 | 7 | |
| 15 | 70 | 2 | |
| 16 | 200 | 7 | |
| 17 | 46 | 1 | |
| 20 | 10 000 | 777 | |
| 21 | 10 000 | 6034 | |
| 22 | 511 | 4 | |
| 23 | 527 | 6 | |
| 24 | 133 | 2 | |
| 26 | 387 | 3 | |
| 28 | 4658 | 105 | |
| 29 | 160 | 3 | |
| 31 | 647 | 9 | |
| 33 | 10 000 | 2697 | |
| 34 | 10 000 | 4144 | |
| 55 | 3538 | 88 | |

What is claimed is:

1. A compound of formula (I):

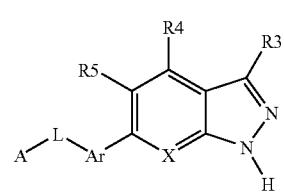

Formula (I)

in which:
1) A is selected from the group consisting of: aryl, heteroaryl, heterocyclyl, substituted aryl, substituted heteroaryl, substituted heterocyclyl, cycloalkyl and substituted cycloalkyl;
2) L is selected from the group consisting of: NH, NH—$SO_2$, $SO_2$NH, NH—$CH_2$, $CH_2$—NH, NH—CO, CO—NH, $CH_2$—CO—NH, NH—CO—$CH_2$, NH—$CH_2$—CO, CO—$CH_2$—NH, NH—CO—NH, NH—CS—NH, NH—CO—O, O—CO—NH, $CH_2$—NH—CO—NH, NH—CO—NH—$CH_2$, and NH—CO—$CH_2$—CO—NH;
3) X is N or NO;
4) R3 is selected from the group consisting of H and NHMR"3, in which M is selected from the group consisting of: a bond, CO, CO—NH, CS, CS—NH and $SO_2$; and in which R"3 is selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl;
5) R4 is selected from the group consisting of: H, halogen, alkyl, substituted alkyl, OR"4, N(R"5)(R"6), and CON(R"5)(R"6), in which R"4 is chosen from H, phenyl, substituted phenyl, alkyl, and substituted alkyl, and in which R"5 and R"6 are independently selected from the group consisting of H, ($C_1$-$C_6$)alkyl, substituted ($C_1$-$C_6$) alkyl, —($C_1$-$C_6$)alkylheterocyclyl, substituted —($C_1$-$C_6$)alkylheterocyclyl, —($C_1$-$C_6$)alkylheteroaryl, substituted —($C_1$-$C_6$)alkylheteroaryl, cycloalkyl, substituted cycloalkyl, heterocyclyl, substituted heterocyclyl, aryl, substituted aryl, heteroaryl, and substituted heteroaryl, or else R"5 and R"6 are linked to one another so as to form a saturated ring having from 4 to 8 ring members containing from 1 to 3 hetero atoms chosen from O, S and N, optionally substituted;
6) R5 is selected from the group consisting of: H, halogen, R'2, CN, O(R'2), OC(O)(R'2), OC(O)N(R'2)(R'3), OS($O_2$)(R'2), N(R'2)(R'3), N=C(R'2)(R'3), N(R'2)C(O)(R'3), N(R'2)C(O)O(R'3), N(R'4)C(O)N(R'2)(R'3), N(R'4)C(S)N(R'2)(R'3), N(R'2)S($O_2$)(R'3), C(O)(R'2), C(O)O(R'2), C(O)N(R'2)(R'3), C(=N(R'3))(R'2), C(=N(OR'3))(R'2), S(R'2), S(O)(R'2), S($O_2$)(R'2), S($O_2$)O(R'2), and S($O_2$)N(R'2)(R'3); in which each R'2, R'3, R'4 is independently selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl, and substituted heterocyclyl; and R'2 and R'3 can be linked to one another so as to form a ring containing from 1 to 3 hetero atoms chosen from O, S and N;

7) Ar is aryl, heterocyclyl, substituted aryl, substituted heterocyclyl, cycloalkyl, substituted cycloalkyl, or heteroaryl, which may optionally be substituted, wherein Ar is chosen from the group consisting of: thiazolyl, thienyl, furyl, pyrrolyl, oxazolyl, isoxazolyl, isothiazolyl, thiadiazolyl, pyrazolyl, imidazolyl, indolyl, indazolyl, benzimidazolyl, benzoxazolyl and benzothiazolyl;

or a pharmaceutically acceptable salt thereof;

provided that, when X is N, R3 is $NH_2$, Ar and A are unsubstituted phenyl, L is NHCO linked in the para-position with respect to Ar, and R5 is H, then R4 is not chosen from:

phenyl, o-chlorophenyl, cinnamyl, α-furfuryl, o-hydroxyphenyl, p-hydroxy-m-methoxyphenyl, p-methylthiophenyl, p-methoxyphenyl, o-nitrophenyl, m-phenoxyphenyl;

and provided that, when X is N, R5 is H, R4 is H, and Ar-L-A is a group

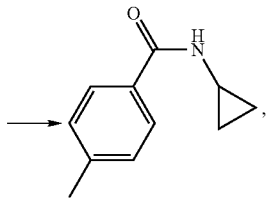

then R3 is not chosen from: amino, acetylamino, [(4-fluorophenyl)carbonyl]amino, (2-methylpropanoyl)amino, -(cyclopentylcarbonyl)amino, propanoylamino, [(4-methylphenyl)carbonyl]amino, {[4-(methyloxy)phenyl]carbonyl}amino, (2-thienylcarbonyl)amino, (methylsulphonyl)amino, -[(4-fluorophenyl)sulphonyl]amino, (ethylsulphonyl) amino, (propylsulphonyl) amino, (3-thienylsulphonyl)amino, [(3,5-dimethyl-4-isoxazolyl)sulphonyl]amino, (2-thienylsulphonyl) amino and (1-methylethyl)amino.

2. A compound according to claim 1 wherein:
1) A is selected from the group consisting of: aryl, heteroaryl, heterocyclyl, cycloalkyl, substituted aryl, substituted heteroaryl, substituted heterocyclyl and substituted cycloalkyl;
2) L is selected from the group consisting of: NH, $NH-SO_2$, $SO_2NH$, $NH-CH_2$, $CH_2-NH$, $CH_2-CO-NH$, $NH-CO-CH_2$, $NH-CH_2-CO$, $CO-CH_2-NH$, $NH-CO-NH$, $NH-CS-NH$, $NH-CO-O$, $O-CO-NH, CH_2-NH-CO-NH$, $NH-CO-NH-CH_2$ and $NH-CO-CH_2-CO-NH$;
3) X is N;
4) R3 is selected from H, NH2 and NHCOR"3, in which R"3 is selected from the group consisting of: H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl;
5) R4 is selected from the group consisting of: H, halogen, alkyl, substituted alkyl, and CON(R"5)(R"6) in which R"5 and R"6 are independently selected from the group consisting of H, $(C_1-C_6)$alkyl, substituted $(C_1-C_6)$alkyl, $-(C_1-C_6)$alkylheterocyclyl, substituted $-(C_1-C_6)$alkylheterocyclyl, $-(C_1-C_6)$alkylheteroaryl, substituted $-(C_1-C_6)$alkylheterocyaryl, cycloalkyl, substituted cycloalkyl, heterocyclyl, substituted heterocyclyl, aryl, substituted aryl, heteroaryl, and substituted heteroaryl or else R"5 and R"6 are linked to one another so as to form a saturated ring having from 4 to 8 ring members containing from 1 to 3 hetero atoms chosen from O, S and N, optionally substituted;
6) R5 is H;
or a pharmaceutically acceptable salt thereof.

3. A compound according to claim 1, wherein Ar is chosen from the group consisting of: thiazolyl, thienyl, furyl, pyrrolyl, oxazolyl, isoxazolyl, isothiazolyl, thiadiazolyl, pyrazolyl, imidazolyl, indolyl, indazolyl, benzimidazolyl, benzoxazolyl and benzothiazolyl; optionally substituted;
or a pharmaceutically acceptable salt thereof.

4. A compound of formula (I):

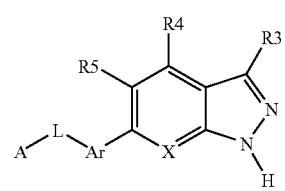

Formula (I)

in which:
1) A is selected from the group consisting of: aryl, heteroaryl, heterocyclyl, substituted aryl, substituted heteroaryl, substituted heterocyclyl, cycloalkyl and substituted cycloalkyl;
2) L is selected from the group consisting of: NH, $NH-SO_2$, $SO_2NH$, $NH-CH_2$, $CH_2-NH$, $NH-CO$, $CO-NH$, $CH_2-CO-NH$, $NH-CO-CH_2$, $NH-CH_2-CO$, $CO-CH_2-NH$, $NH-CO-NH$, $NH-CS-NH$, $NH-CO-O$, $O-CO-NH$, $CH_2-NH-CO-NH$, $NH-CO-NH-CH_2$, and $NH-CO-CH_2-CO-NH$;
3) X is N or NO;
4) R3 is selected from the group consisting of H and NHMR"3, in which M is selected from the group consisting of: a bond, CO, CO—NH, CS, CS—NH and $SO_2$; and in which R"3 is selected from the group consisting of H, alkyl, alkylene, alkynyl, aryl, heteroaryl, cycloalkyl, heterocyclyl, substituted alkyl, substituted alkylene, substituted alkynyl, substituted aryl, substituted cycloalkyl and substituted heterocyclyl;
5) R4 is selected from the group consisting of H, halogen, alkyl, substituted alkyl, OR"4, N(R"5)(R"6), and CON(R"5)(R"6), in which R"4 is chosen from H, phenyl, substituted phenyl, alkyl, and substituted alkyl, and in which R"5 and R"6 are independently selected from the group consisting of H, $(C_1-C_6)$alkyl, substituted $(C_1-C_6)$alkyl, $-(C_1-C_6)$alkylheterocyclyl, substituted $-(C_1-C_6)$alkylheterocyclyl, $-(C_1-C_6)$alkylheteroaryl, substituted $-(C_1-C_6)$alkylheteroaryl, cycloalkyl, substituted cycloalkyl, heterocyclyl, substituted heterocyclyl, aryl, substituted aryl, heteroaryl, and substituted heteroaryl, or else R"5 and R"6 are linked to one another so as to form a saturated ring having from 4 to 8 ring members containing from 1 to 3 hetero atoms chosen from O, S and N, optionally substituted;
6) R5 is selected from the group consisting of: H, halogen, R'2, CN, O (R'2), OC(O )(R'2), OC(O)N(R'2)(R'3), $OS(O_2)(R'2)$, N(R'2)(R'3), N=C(R'2)(R'3), N(R'2)C(O)(R'3), N(R'2)C(O)O(R'3), N(R'4)C(O)N(R'2)(R'3), N(R'4)C(S)N(R'2)(R'3), $N(R'2)S(O_2)(R'3)$, C(O)(R'2), C(O)O(R'2), C(O)N(R'2)(R'3), C(=N(R'3))(R'2), C(=N(OR'3))(R'2), S(R'2), S(O)(R'2), S(O$_2$)(R'2), S(O$_2$)O(R'2), and S(O$_2$)N(R'2)(R'3); in which each R'2, R'3, R'4 is independently selected from the group consisting of H, alkyl, alklene alkenyl, aryl, heteroaryl, cycloalkyl, heterocyclyl, substituted alkyl, substituted alkylene, substituted alkynyl, substituted aryl, substituted heteroaryl, substituted cycloalkyl, and substituted heterocyclyl; and R'2 and R'3 can be linked to one another so as to form a ring containing from 1 to 3 hetero atoms chosen from O, S and N;

7) Ar is aryl, and wherein Ar-L-A is:

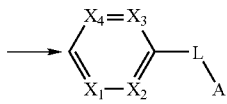

in which each X1, X2, X3 and X4 is independently chosen from C—R'5, in which R'5 has the same definition as R5 or a pharmaceutically acceptable salt thereof;

provided that, when X is N, R3 is NH$_2$, Ar and A are unsubstituted phenyl, L is NHCO linked in the para-position with respect to Ar, and R5 is H, then R4 is not chosen from:

phenyl, o-chlorophenyl, cinnamyl, α-furfuryl, o-hydroxyphenyl, p-hydroxy-m-methoxyphenyl, p-methylthiophenyl, p-methoxyphenyl, o-nitrophenyl, m-phenoxyphenyl;

and provided that, when X is N, R5 is H, R4 is H, and Ar-L-A is a group

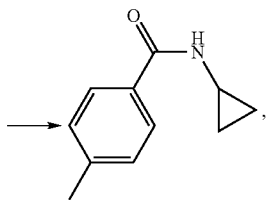

then R3 is not chosen from: amino, acetylamino, [(4-fluorophenyl)carbonyl]amino, (2-methylpropanoyl)amino, -(cyclopentylcarbonyl)amino, propanoylamino, [(4-methylphenyl)carbonyl]amino, {[4-(methyloxy)phenyl]carbonyl}amino, (2-thienylcarbonyl)amino, (methylsulphonyl)amino, -[(4-fluorophenyl)sulphonyl]amino, (ethylsulphonyl)amino, (propylsulphonyl)amino, (3-thienylsulphonyl)amino, [(3,5-dimethyl-4-isoxazolyl)sulphonyl]amino, (2-thienylsulphonyl)amino and (1-methylethyl)amino.

5. A compound according to claim 1, wherein L-A is selected from the group consisting of NH—CO—NH-A and NH—SO$_2$-A;
or a pharmaceutically acceptable salt thereof.

6. A compound according to claim 1, wherein A is selected from the group consisting of: phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl; optionally substituted;
or a pharmaceutically acceptable salt thereof.

7. A compound according to claim 6, wherein A is selected from the group consisting of: phenyl, pyrazolyl and isoxazolyl; optionally substituted;
or a pharmaceutically acceptable salt thereof.

8. A compound according to claim 1, wherein A is substituted with a first substituent selected from the group consisting of halogen, alkyl, alkylene, alkynyl, aryl, heteroaryl, O-alkyl, O-aryl, O-heteroaryl, S-alkyl, S-aryl, and S-heteroaryl, each being optionally substituted with one or more substituents chosen from (C$_1$-C$_3$)alkyl, halogen and O—(C$_1$-C$_3$)alkyl;
or a pharmaceutically acceptable salt thereof.

9. A compound according to claim 8, wherein A is substituted with a second substituent selected from the group consisting of F, Cl, Br, I, OH, SH, SO$_3$M, COOM, CN, NO$_2$, CON(R8)(R9), N(R8)CO(R9), (C$_1$-C$_3$)alkyl-OH, (C$_1$-C$_3$)alkyl-N(R8)(R9), (C$_1$-C$_3$)alkyl-(R10), (C$_1$-C$_3$)alkyl-COOH, and N(R8)(R9); in which R8 and R9 are independently chosen from H, (C$_1$-C$_3$)alkyl, halogenated (C$_1$-C$_3$)alkyl, (C$_1$-C$_3$)alkylOH, (C$_1$-C$_3$)alkyl-O(C$_1$-C$_3$)alkyl,(C$_1$-C$_3$)alkylNH$_2$, (C$_1$-C$_3$)alkylN(R8)(R9), (C$_1$-C$_3$)alkylCOOM, and (C$_1$-C$_3$)alkylSO$_3$M; in which, when R8 and R9 are simultaneously different from H, they can be linked so as to form a ring having from 5 to 7 ring members containing from 1 to 3 hetero atoms; in which M is H or a cation of an alkali metal chosen from Li, Na and K; and in which R10 is H or an optionally substituted, non-aromatic heterocycle containing 2 to 7 carbon atoms and 1 to 3 hetero atoms chosen from N, O and S;
or a pharmaceutically acceptable salt thereof.

10. A compound according to claim 1, wherein A is chosen from phenyl, pyrazolyl and isoxazolyl; optionally substituted with halogen, (C$_1$-C$_4$)alkyl, halogenated (C$_1$-C$_3$)alkyl, O—(C$_1$-C$_4$)alkyl, S—(C$_1$-C$_4$)alkyl, halogenated O—(C$_1$-C$_4$)alkyl, and halogenated S—(C$_1$-C$_4$)alkyl, and in that, when A is disubstituted, the two substituents of A can form a ring having from 5 to 7 ring members containing from 0 to 3 hetero atoms chosen from O, N and S;
or a pharmaceutically acceptable salt thereof.

11. A compound according to claim 1, wherein R4 is H or CON(R"5)(R"6), with R"5 and R"6 as defined in claim 1;
or a pharmaceutically acceptable salt thereof.

12. A compound selected from the group consisting of:
1-[4-(3-amino-1H-pyrazolo[3,4-b]pyridin-6-yl)phenyl]-3-(2-fluoro-5-trifluoromethyl-pheny)urea;
thiophene-3-carboxylic acid(6-{4-[3-(2-fluoro-5-trifluoromethylphenyl)ureido]phenyl}-1H-pyrazolo[3,4-b]pyridin-3-yl)amide;
6-{2-[3-(2-fluoro-5-trifluoromethylphenyl)ureido]thiazol-5-yl}-1H-pyrazolo[3,4-b]pyridine-4-carboxylic acid(2-morpholin-4-ylethyl)amide trifluoroacetate;
6-{4-[3-(2-fluoro-5-trifluoromethylphenyl)ureido]phenyl}-1H-pyrazolo[3,4-b]pyridine-4-carboxylic acid amide;
6-{4-[3-(2-fluoro-5-trifluoromethylphenyl)ureido]phenyl}-1H-pyrazolo[3,4-b]pyridine-4-carboxylic acid methylamide;
6-{4-[3-(2-fluoro-5-trifluoromethylphenyl)ureido]phenyl}-1H-pyrazolo[3,4-b]pyridine-4-carboxylic acid(2-morpholin-4-ylethyl)amide;
6-[2-(3-phenylureido)thiazol-5-yl]-1H-pyrazolo[3,4-b]pyridine-4-carboxylic acid (2-morpholin-4-ylethyl) amide;
6-{2-[3(2-fluoro-5-trifluoromethylpheny)ureido]thiazol-5-yl}-1H-pyrazolo[3,4-b]pyridine-4-carboxylic acid amide;
6-{2-[3-(2-fluoro-5-trifluoromethylpheny)ureido]thiazol-5-yl}-1H-pyrazolo[3,4-b]pyridine-4-carboxylic acid methylamide;

6-{2-[3-(2-fluoro-5-trifluoromethylphenyl)ureido]thiazol-5-yl}-1H-pyrazolo[3,4-b]pyridine-4-carboxylic acid(2-dimethylaminoethyl)amide;

6-{2-[3-(2-fluoro-5-trifluoromethylphenyl)ureido]thiazol-5-yl}-1H-pyrazolo[3,4-b]pyridine-4-carboxylic acid(3-dimethylamino-2,2-dimethylpropyl)amide;

6-{2-[3-(2-fluoro-5-trifluoromethylphenyl)ureido]thiazol-5-yl}-1H-pyrazolo[3,4-b]pyridine-4-carboxylic acid [2-(3H-imidazol-4-yl)ethyl]amide;

1-(2-fluoro-5-trifluoromethylphenyl)-3-{5-[4-(morpholine-4-carbonyl)-1H-pyrazolo[3,4-b]pyridin-6-yl]thiazol-2-yl}urea;

1-(2-fluoro-5-trifluoromethylphenyl)-3-{5-[4-(piperazine-1-carbonyl)-1H-pyrazolo[3,4-b]pyridin-6-yl]-thiazol-2-yl}urea;

1-(2-fluoro-5-trifluoromethylphenyl)-3-{5-[4-(4-methylpiperazine-1-carbonyl)-1H-pyrazolo[3,4-b]pyridin-6-yl]-thiazol-2-yl}urea;

6-{2-[3-(2-fluoro-5-trifluoromethylphenyl)ureido]thiazol-5-yl}-1H-pyrazolo[3,4-b]pyridine-4-carboxylic acid(2,3-dihydroxypropyl)amide;

6-{2-[3-(2-fluoro-5-trifluoromethylphenyl)ureido]thiazol-5-yl}-1H-pyrazolo[3,4-b]pyridine-4-carboxylic acid(2H-pyrazol-3-yl)amide;

6-{6-[3-(2-fluoro-5-trifluoromethylphenyl)ureido]pyridin-3 -yl}-1H-pyrazolo[3,4-b]pyridine-4-carboxylic acid methylamide;

6-{6-[3-(2-fluoro-5-trifluoromethylphenyl)ureido]pyridin-3-yl}-1H-pyrazolo[3,4-b]pyridine-4-carboxylic acid(2-morpholin-4-ylethyl)amide;

6-{2-[3-(2-fluoro-5-trifluoromethylphenyl)ureido]thiazol-5-yl}-1H-pyrazolo[3,4-b]pyridine-4-carboxylic acid(3-morpholin-4-ylpropyl)amide;

6-{2-[3-(2-fluoro-5-trifluoromethylphenyl)ureido]thiazol-5-yl}-1H-pyrazolo[3,4-b]pyridine-4-carboxylic acid(2-piperazin-1-ylethyl)amide;

6-{2-[3-(2-fluoro-5-trifluoromethylphenyl)ureido]thiazol-5-yl}-1H-pyrazolo[3,4-b]pyridine-4-carboxylic acid(2-piperidin-4-ylethyl)amide;

6-{2-[3-(2-fluoro-5-trifluoromethylphenyl)ureido]thiazol-5-yl}-1H-pyrazolo[3,4-b]pyridine-4-carboxylic acid [3-(4-methylpiperazin-1-yl)propyl]amide;

6-{2-[3-(2-fluoro-5-trifluoromethylphenyl)ureido]thiazol-5-yl}-1H-pyrazolo[3,4-b]pyridine-4-carboxylic acid(2-hydroxyethyl)amide;

6-{2-[3-(2-fluoro-5-trifluoromethylphenyl)ureido]thiazol-5-yl}-1H-pyrazolo[3,4-b]pyridine-4-carboxylic acid(2-methoxyethyl)amide;

6-{2-[3-(2-fluoro-5-trifluoromethylphenyl)ureido]thiazol-5-yl}-1H-pyrazolo[3,4-b]pyridine-4-carboxylic acid(pyridin-4-ylmethyl)amide;

6-{2-[3-(2-fluoro-5-trifluoromethylphenyl)ureido]thiazol-5-yl}-1H-pyrazolo[3,4-b]pyridine-4-carboxylic acid(pyridin-2-ylmethyl)amide;

1-(2-fluoro-5-trifluoromethylphenyl)-3-{5-[4-(2-hydroxymethylpyrrolidine-1-carbonyl)-1H-pyrazolo[3,4-b]pyridin-6-yl]thiazol-2-yl}urea;

6-{2-[3-(2-fluoro-5-trifluoromethylphenyl)ureido]thiazol-5-yl}-1H-pyrazolo[3,4-b]pyridine-4-carboxylic acid [3-(2-hydroxymethylpyrrolidin-1-yl)propyl] amide;

1-(2-fluoro-5-trifluoromethylphenyl)-3-{5-[4-(2-hydroxymethylpiperazine-1-carbonyl)-1H-pyrazolo[3,4-b]pyridin-6-yl]thiazol-2-yl}urea;

6-{3-[3-(2-fluoro-5-trifluoromethylphenyl)ureido]phenyl}-1H-pyrazolo[3,4-b]pyridine-4-carboxylic acid methylamide;

6-{3-[3-(2-fluoro-5-trifluoromethylphenyl)ureido]phenyl}-1H-pyrazolo [3,4-b]pyridine-4-carboxylic acid(2-morpholin-4-ylethyl)amide;

6-{5-[3-(2-fluoro-5-trifluoromethylphenyl)ureido]isoxazol-3-yl}-1H-pyrazolo[3,4-b]pyridine-4-carboxylic acid(2-morpholin-4-ylethyl)amide;

6-{2-[3-(2-fluoro-5-trifluoromethylphenyl)ureido]thiazol-5-yl}-1H-pyrazolo[3,4-b]pyridine-4-carboxylic acid(pyridin-3-ylmethyl)amide;

6-{2-[3-(2-fluoro-5-trifluoromethylphenyl)ureido]thiazol-5-yl}-1H-pyrazolo [3,4-b]pyridine-4-carboxylic acid [2-(4-methylpiperazin-1-yl)ethyl]amide;

6-{5-[3-(2-fluoro-5-trifluoromethylphenyl)ureido][1,3,4]thiadiazol-2-yl}-1H-pyrazolo[3,4-b]pyridine-4-carboxylic acid(2-morpholin-4-ylethyl)amide;

6-{5-[3-(2-fluoro-5-trifluoromethylphenyl)ureido]thiophen-2-yl}-1H-pyrazolo [3,4-b]pyridine-4-carboxylic acid(2-morpholin-4-ylethyl)amide;

6-{2-[3-(3-trifluoromethylphenyl)ureido]thiazol-5-yl}-1H-pyrazolo[3,4-b]pyridine-4-carboxylic acid(2-morpholin-4-ylethyl)amide;

6-{2-[3-(3-trifluoromethylsulphanylphenyl)ureido]thiazol-5-yl}-1H-pyrazolo[3,4-b]pyridine-4-carboxylic acid(2-morpholin-4-ylethyl)amide;

6-{2-[3-(3-fluoro-5-trifluoromethylphenyl)ureido]thiazol-5-yl}-1H-pyrazolo[3,4-b]pyridine-4-carboxylic acid(2-morpholin-4-ylethyl)amide;

6-{2-[3-(4-fluoro-3-trifluoromethylphenyl)ureido]thiazol-5-yl}-1H-pyrazolo[3,4-b]pyridine-4-carboxylic acid(2-morpholin-4-ylethyl)amide;

6-{2-[3-(2-chlorophenyl)ureido]thiazol-5-yl}-1H-pyrazolo[3,4-b]pyridine-4-carboxylic acid (2-morpholin-4-ylethyl)amide;

6-{2-[3-(3-chlorophenyl)ureido]thiazol-5-yl}-1H-pyrazolo[3,4-b]pyridine-4-carboxylic acid (2-morpholin-4-ylethyl)amide;

6-{2-[3-(2-fluoro-3-trifluoromethylphenyl)ureido]thiazol-5-yl}-1H-pyrazolo[3,4-b]pyridine-4-carboxylic acid(2-morpholin-4-ylethyl)amide;

6-{2-[3-(3-chloro-4-fluorophenyl)ureido]thiazol-5-yl}-1H-pyrazolo[3,4-b]pyridine-4-carboxylic acid(2-morpholin-4-ylethyl)amide;

6-{2-[3-(2-methoxyphenyl)ureido]thiazol-5-yl}-1H-pyrazolo[3,4-b]pyridine-4-carboxylic acid(2-morpholin-4-ylethyl)amide;

6-{2-[3-(2,5-difluorophenyl)ureido]thiazol-5-yl}-1H-pyrazolo[3,4-b]pyridine-4-carboxylic acid(2-morpholin-4-ylethyl)amide;

6-{2-[3-(2,4-difluorophenyl)ureido]thiazol-5-yl}-1H-pyrazolo[3,4-b]pyridine-4-carboxylic acid(2-morpholin-4-ylethyl)amide;

6-{2-[3-(4-trifluoromethylphenyl)ureido]thiazol-5-yl}-1H-pyrazolo[3,4-b]pyridine-4-carboxylic acid(2-morpholin-4-ylethyl)amide;

6-{2-[3-(2-fluorophenyl)ureido]thiazol-5-yl}-1H-pyrazolo[3,4-b]pyridine-4-carboxylic acid (2-morpholin-4-ylethyl)amide;

6-{2-[3-(3,4-dichlorophenyl)ureido]thiazol-5-yl}-1H-pyrazolo[3,4-b]pyridine-4-carboxylic acid(2-morpholin-4-ylethyl)amide;

6-{2-[3-(4-trifluoromethoxyphenyl)ureido]thiazol-5-yl}-1H-pyrazolo [3,4-b]pyridine-4-carboxylic acid(2-morpholin-4-ylethyl)amide;

6-{2-[3-(3-cyanophenyl)ureido]thiazol-5-yl}-1H-pyrazolo[3,4-b]pyridine-4-carboxylic acid (2-morpholin-4-ylethyl)amide;

6-{2-[3-(3-methoxyphenyl)ureido]thiazol-5-yl}-1H-pyrazolo [3,4-b]pyridine-4-carboxylic acid(2-morpholin-4-ylethyl)amide;

6-{2-[3-(4-chlorophenyl)ureido]thiazol-5-yl}-1H-pyrazolo[3,4-b]pyridine-4-carboxylic acid (2-morpholin-4-ylethyl)amide; and 6-{2-[3-(2,4-dimethoxyphenyl)ureido]thiazol-5-yl}-1H-pyrazolo [3,4-b]pyridine-4-carboxylic acid(2-morpholin-4-ylethyl)amide;

or a pharmaceutically acceptable salt thereof.

13. A compound according to claim 1, selected from the group consisting of:
N-[4-(4-(2-morpholin-4-ylethyl)aminocarbonyl-1H-pyrazolo[3,4-b]pyridin-6-yl)phenyl]-3-chlorobenzenesulphonamide;
N-[4-(4-(piperazine-1-carbonyl)-1H-pyrazolo[3,4-b]pyridin-6-yl)phenyl]-2,3-dichlorobenzenesulphonamide;
N-[4-(4-methylaminocarbonyl-1H-pyrazolo[3,4-b]pyridin-6-yl)phenyl]-2-chloro-4-trifluoromethylbenzenesulphonamide;
N-[4-(4-methylaminocarbonyl-1H-pyrazolo[3,4-b]pyridin-6-yl)phenyl]-4-fluorobenzenesulphonamide;
N-[4-(3-amino-1H-pyrazolo[3,4-b]pyridin-6-yl)phenyl]-2,3-dichlorobenzenesulphonamide; and
N-[4-(3-amino-4-methylaminocarbonyl-1H-pyrazolo[3,4-b]pyridin-6-yl)phenyl]-2,3-dichlorobenzenesulphonamide;

or a pharmaceutically acceptable salt thereof.

14. A pharmaceutical composition comprising a compound according to claim 1 or a pharmaceutically acceptable salt thereof, in combination with a pharmaceutically acceptable excipient.

15. A pharmaceutical composition comprising a compound according to claim 12 or a pharmaceutically acceptable salt thereof, in combination with a pharmaceutically acceptable excipient.

16. A method for inhibiting a reaction catalyzed by one or more kinases, said method comprising contacting said kinase with a compound according to claim 1, or a pharmaceutically acceptable salt thereof, wherein the kinase is chosen from FAK, KDR and Tie2.

17. A method for treating a pathological condition comprising administering to a patient in need thereof a therapeutically effective amount of a compound according to claim 1, wherein the pathological condition is chosen from rheumatoid arthritis, osteoarthritis and/or its associated pain, inflammatory diseases of the intestine, eye pathologies, diabetic retinopathies, chronic inflammation, psoriasis, Kaposi's sarcoma and infantile haemangioma.

18. The method according to claim 17 further comprising the administration of an anticancer agent.

19. A compound of the formula (II):

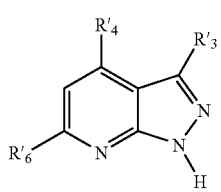

(II)

in which R'$_4$ represents R4 or H, —COOH or —COO—(C$_1$-C$_6$)alkyl, R'$_3$ represents H, —NH$_2$ or —NHCO-thienyl, and R'$_6$ represents an —Ar-NH$_2$ group or an Ar-L-A group where L and A are as defined in claim 1 and Ar is aryl, heteroaryl, heterocyclyl, substituted aryl, substituted heteroaryl, substituted heterocyclyl, cycloalkyl or substituted cycloalkyl.

20. A compound of formula (III):

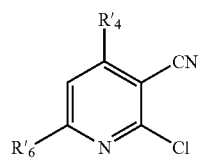

(III)

in which R'$_4$ represents R4 or H, —COOH or —COO—(C$_1$-C$_6$)alkyl, and R'$_6$ represents an —Ar—NH$_2$ group or an Ar-L-A group where, L and A are as defined in claim 1, and Ar is selected from the group consisting of aryl, heteroaryl, heterocyclyl, substituted aryl, substituted heteroaryl, substituted heterocyclyl, cycloalkyl and substituted cycloalkyl.

21. The compound according to claim 3 wherein
1) A is selected from the group consisting of: aryl, heteroaryl, heterocyclyl, substituted aryl, substituted heteroaryl, substituted heterocyclyl, cycloalkyl and substituted cycloalkyl;
2) L is selected from the group consisting of: NH, NH—SO$_2$, SO$_2$NH, NH—CH$_2$, CH$_2$—NH, CH$_2$—CO—NH, NH—CO—CH$_2$, NH—CH$_2$—CO, CO—CH$_2$—NH, NH—CO—NH, NH—CS—NH, NH—CO—O, O—CO—NH, CH$_2$—NH—CO—NH, NH—CO—NH—CH$_2$, and NH—CO—CH$_2$—CO—NH;
3) X is N;
4) R3 is selected from the group consisting of H, NH$_2$ and NHMR"3, in which R"3 is selected from the group consisting of H, alkyl, alkylene, alkynyl, aryl, heteroaryl, cycloalkyl, heterocyclyl, substituted alkyl, substituted alkylene, substituted alkynyl, substituted aryl, substituted heteroaryl, substituted cycloalkyl and substituted heterocyclyl;
5) R4 is selected from the group consisting of: H, halogen, alkyl, substituted alkyl, and CON(R"5)(R"6), in which R"5 and R"6 are independently selected from the group consisting of H, (C$_1$-C$_6$)alkyl, substituted (C$_1$-C$_6$)alkyl, —(C$_1$-C$_6$)alkylheterocyclyl, substituted —(C$_1$-C$_6$)alkylheterocyclyl, —(C$_1$-C$_6$)alkylheteroaryl, substituted —(C$_1$-C$_6$)alkylheteroaryl, cycloalkyl, substituted cycloalkyl, heterocyclyl, substituted heterocyclyl, aryl, substituted aryl, heteroaryl, and substituted heteroaryl, or else R"5 and R"6 are linked to one another so as to form a saturated ring having from 4 to 8 ring members containing from 1 to 3 hetero atoms chosen from O, S and N, optionally substituted;
6) R5 is H
or a pharmaceutically acceptable salt thereof.

22. the compound according to claim 3 wherein L-A is selected from the group consisting of NH—CO—NH-A and NH—SO$_2$-A;
or a pharmaceutically acceptable salt thereof.

23. The compound according to claim 3 wherein A is selected from the group consisting of: phenyl, pyridyl, pyrimidyl, thienyl, furyl, pyrrolyl, oxazolyl, thiazolyl, isoxazolyl, isothiazolyl, pyrazolyl, imidazolyl, indolyl, indazolyl, benzimidazolyl, benzoxazolyl and benzothiazolyl; optionally substituted;
or a pharmaceutically acceptable salt thereof.

24. The compound according to claim 23 wherein A is selected from the group consisting of: phenyl, pyrazolyl and isoxazolyl; optionally substituted;

or a pharmaceutically acceptable salt thereof.

25. The compound according to claim 3, A is substituted with a first substituent selected from the group consisting of halogen, alkyl, alkylene, alkynyl, aryl, heteroaryl, O-alkyl, O-aryl, O-heteroaryl, S-alkyl, S-aryl, and S-heteroaryl, each being optionally substituted with one or more substituents chosen from $(C_1-C_3)$alkyl, halogen and O—$(C_1-C_3)$alkyl;

or a pharmaceutically acceptable salt thereof.

26. The compound according to claim 25 wherein A is substituted with a second substituent selected from the group consisting of F, Cl, Br, I, OH, SH, $SO_3M$, COOM, CN, $NO_2$, CON(R8)(R9), N(R8)CO(R9), $(C_1-C_3)$alkyl-OH, $(C_1-C_3)$alkyl-N(R8)(R9), $(C_1-C_3)$alkyl-(R10), $(C_1-C_3)$alkyl-COOH, and N(R8)(R9); in which R8 and R9 are independently chosen from H, $(C_1-C_3)$alkyl, halogenated $(C_1-C_3)$alkyl, $(C_1-C_3)$alkylOH, $(C_1-C_3)$alkyl-O$(C_1-C_3)$alkyl, $(C_1-C_3)$alkylNH$_2$, $(C_1-C_3)$alkylN(R8)(R9), $(C_1-C_3)$alkylCOOM, and $(C_1-C_3)$alkylSO$_3$M; in which, when R8 and R9 are simultaneously different from H, they can be linked so as to form a ring having from 5 to 7 ring members containing from 1 to 3 hetero atoms; in which M is H or a cation of an alkali metal chosen from Li, Na and K; and in which R10 is H or an optionally substituted, non-aromatic heterocycle containing 2 to 7 carbon atoms and 1 to 3 hetero atoms chosen from N, O and S;

or a pharmaceutically acceptable salt thereof.

27. The compound according to claim 3 wherein A is chosen from phenyl, pyrazolyl and isoxazolyl; optionally substituted with halogen, $(C_1-C_4)$alkyl, halogenated $(C_1-C_3)$alkyl, O—$(C_1-C_4)$alkyl, S—$(C_1-C_4)$alkyl, halogenated O—$(C_1-C_4)$alkyl, and halogenated S—$(C_1-C_4)$alkyl, and in that, when A is disubstituted, the two substituents of A can form a ring having from 5 to 7 ring members containing from 0 to 3 hetero atoms chosen from O, N and S;

or a pharmaceutically acceptable salt thereof.

28. The compound according to claim 3, wherein R4 is H or CON(R"5)(R"6), or a pharmaceutically acceptable salt thereof.

29. A pharmaceutical composition comprising a compound according to claim 3 or a pharmaceutically acceptable salt thereof, in combination with a pharmaceutically acceptable excipient.

30. A method for inhibiting a reaction catalyzed by one or more kinases, said method comprising contacting said kinase with a compound according to claim 3, or a pharmaceutically acceptable salt thereof, wherein the kinase is chosen from FAK, KDR and Tie2.

31. A method for treating a pathological condition comprising administering to a patient in need thereof a therapeutically effective amount of a compound according to claim 3, wherein the pathological condition is chosen from rheumatoid arthritis, osteoarthritis and/or its associated pain, inflammatory diseases of the intestine, eye pathologies, diabetic retinopathies, chronic inflammation, psoriasis, Kaposi's sarcoma and infantile haemangioma.

32. The method according to claim 31 further comprising the administration of an anticancer agent.

* * * * *